(12) United States Patent
Feygin et al.

(10) Patent No.: US 6,742,549 B1
(45) Date of Patent: Jun. 1, 2004

(54) METHOD AND APPARATUS FOR QUASI-CONTINUOUS AND QUASI-SIMULTANEOUS DISPENSING

(75) Inventors: Ilya Feygin, Mountainside, NJ (US); John M. Newsam, San Diego, CA (US)

(73) Assignee: Fqubed, San Diego, CA (US)

( * ) Notice: Subject to any disclaimer, the term of this patent is extended or adjusted under 35 U.S.C. 154(b) by 0 days.

(21) Appl. No.: 10/348,769

(22) Filed: Jan. 21, 2003

(51) Int. Cl.⁷ .................................................. B65B 3/00
(52) U.S. Cl. ......................... 141/9; 141/100; 141/102; 141/104
(58) Field of Search .......................... 141/9, 100–104, 141/236–238, 242, 243; 222/129.1, 129.2, 129.3, 129.4, 132, 144.5

(56) References Cited

U.S. PATENT DOCUMENTS

| | | | | |
|---|---|---|---|---|
| 2,757,839 A | * | 8/1956 | Carew | 141/102 |
| 4,426,021 A | * | 1/1984 | Rosenthal | 222/129.1 |
| 4,827,993 A | * | 5/1989 | Ito et al. | 141/83 |
| 5,168,905 A | * | 12/1992 | Phallen | 141/1 |
| 5,566,733 A | * | 10/1996 | Germain | 141/192 |
| 6,063,339 A | * | 5/2000 | Tisone et al. | 422/67 |
| 6,637,471 B2 | * | 10/2003 | Luehrsen et al. | 141/83 |
| 6,641,517 B2 | * | 11/2003 | Anderson | 494/37 |
| 2003/0209283 A1 | * | 11/2003 | Fabry | 141/237 |

* cited by examiner

Primary Examiner—J. Casimer Jacyna
(74) Attorney, Agent, or Firm—DeMont & Breyer, LLC

(57) ABSTRACT

A system and for creating multiple mixtures is disclosed. The illustrative system described herein includes dispensing elements that are moved into alignment with various receivers (or vice versa) to deliver ingredients. In some embodiments, the system requires only one dispensing element (e.g., valve, nozzle, orifice, etc.) per ingredient dispensed, irrespective of the number of receivers in the system. In accordance with the principles of this invention, the system is operated such that a plurality of ingredients are incrementally added to the receivers. Incremental addition is performed in such a way that, from the "perspective" of the mixture being formed, the ingredients are added quasi-continuously (i.e., a near-continuous flow of an ingredient) or quasi-simultaneously (i.e., all ingredients are added at nearly the same time), or both.

34 Claims, 12 Drawing Sheets

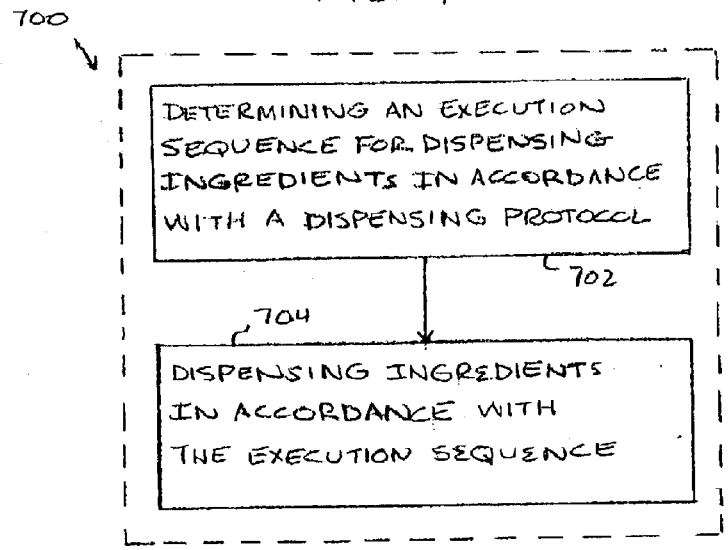
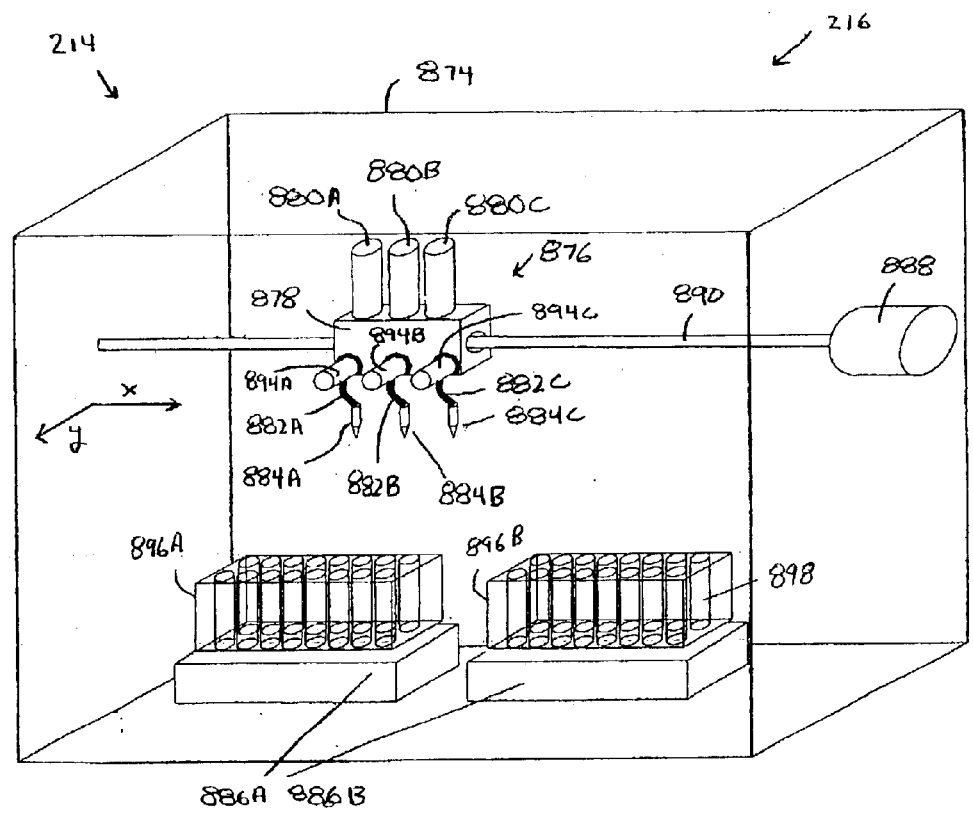

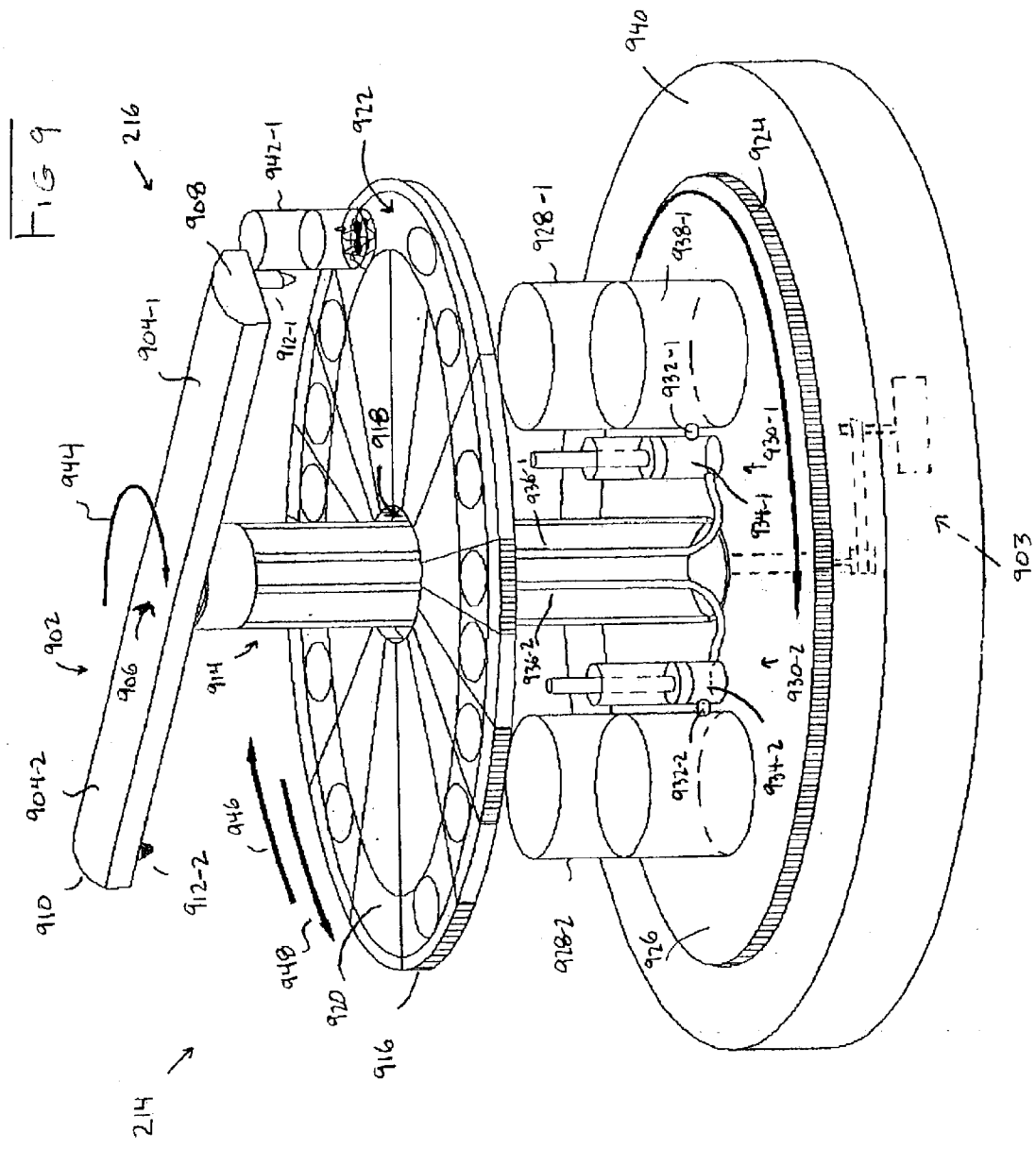

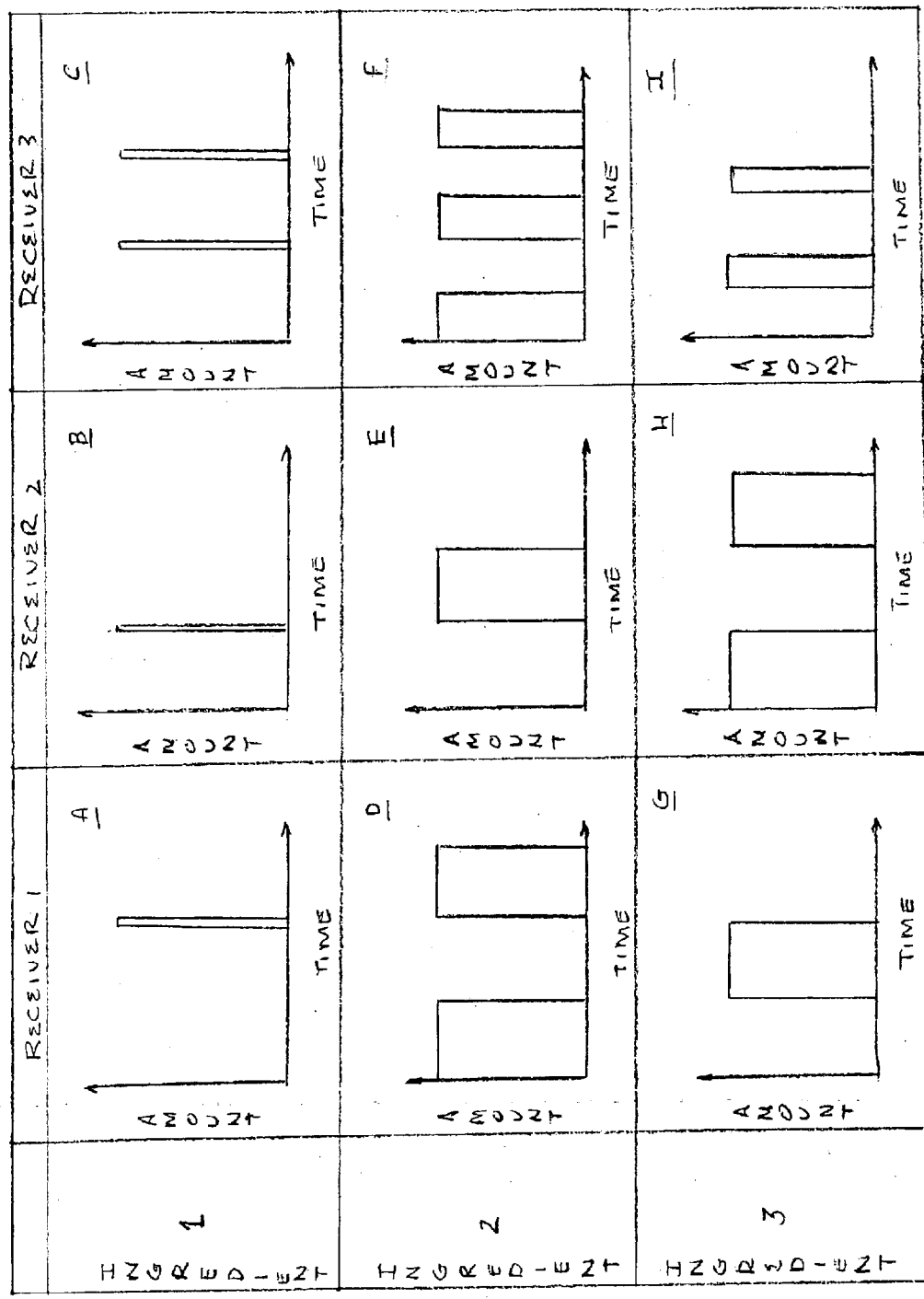

METHOD AND APPARATUS FOR QUASI-CONTINUOUS AND QUASI-SIMULTANEOUS DISPENSING

FIELD OF THE INVENTION

The present invention relates to a method and apparatus for dispensing each of two or more feeds into a plurality of vessels.

BACKGROUND OF THE INVENTION

In many industrial and laboratory applications, it is common to combine two or more ingredients during the course of processing or fabrication operations. In laboratory applications, the ingredients are typically combined in receiver (e.g., flask, test tube, wells in a microtitre plate, etc.) in precise proportions and under selected conditions.

In some applications, such as in the development of polymers, the manner in which the ingredients are combined is important. For example, it is often desirable or necessary for the ingredients to be simultaneously added to the receiver. In some cases, this is necessary to prevent undesired reactions from occurring.

In the development of polymers, as well as many other products (e.g., pharmaceuticals, nutraceuticals, cosmeceuticals, etc.), a preference exists for delivery systems that are capable of rapidly and efficiently producing and/or screening samples. This high-speed capability, which hastens development efforts, is commonly referred to as "high-throughput screening," "high-throughput experimentation," or "high-throughput testing," or by the respective acronyms "HTS," "HTE," or "HTT" (these monikers are synonymous). An HTE-capable ingredient delivery system must be able to provide multiple copies or multiple permutations of a sample.

FIG. 1 depicts a typical HTE-capable delivery system for creating mixtures of ingredients for the development of polymers or other products. System 100 is able to simultaneously combine three ingredients, in specific proportions, to produce a mixture F (or permutations thereof) in each of three receivers 112-A, 112-B, and 112-C (collectively "receivers 112"). A HTE-capable system more typically includes a minimum of eight, and more likely 12, 16 or 24 receivers. But for the purpose of simplifying FIG. 1 and the accompanying discussion, only three receivers are depicted.

System 100 includes reservoirs 102-1, 102-2, and 102-3 (collectively "reservoirs 102,") which contain respective ingredients I-1, I-2, I-3 (collectively "ingredients I"). The reservoirs are maintained under positive pressure, via pressurized gas source 104, so that the ingredients I can be delivered to receivers 112.

Each reservoir 102 has three conduits 106 that lead to three valves 108. The three valves, in turn, feed the three receivers 112. With this arrangement, the ingredient I in a given reservoir 102 can be delivered to each of the three receivers 112-1, 112-2, and 112-3.

More particularly, and with respect to reservoir 102-1, one of conduits 106-1 connects that reservoir to valve 108-$A_1$, another of conduits 106-1 connects reservoir 102-1 to valve 108-$B_1$, and the third conduit 106-1 connects reservoir 102-1 to valve 108-$C_1$. With respect to reservoir 102-2, one of conduits 106-2 connects that reservoir to valve 108-$A_2$, another of conduits 106-2 connects that reservoir to valve 108-$B_2$, and the third conduit 106-2 connects reservoir 102-2 to valve 108-$C_2$. And, with respect to reservoir 102-3, one of conduits 106-3 connects that reservoir to valve 108-$A_3$, another of conduits 106-3 connects that reservoir to valve 108-$B_3$, and the third conduit 106-3 connects reservoir 102-3 to valve 108-$C_3$.

As follows from the foregoing description, and as indicated in FIG. 1, each receiver 112 is served by three valves. Specifically, valves 108-$A_1$, 108-$A_2$, 108-$A_3$ control the flow of respective ingredients I-1, I-2, I-3 into receiver 112-A. Similarly, valves 108-$B_2$, 108-$B_2$, 108-$B_3$ control the flow of respective ingredients I-1, I-2, I-3 into receiver 112-8 and valves 108-$C_1$, 108-$C_2$, 108-$C_3$ control flow of respective ingredients I-1, I-2, I-3 into receiver 112-C.

Valves 108, which can be proportional valves, or which are otherwise time or flow controlled, are capable of providing precise control over parameters such as flow pressure, flow rate and the like. Open or closed-loop control systems are typically associated with each valve to ensure that the proper amount of each ingredient is delivered to each receiver 112.

System 100 depicts a classic, combinatorial-type, liquid-dispensing arrangement. The combinatorial-type arrangement enables all ingredients I (i.e., I-1, I-2, I-3) to be delivered simultaneously to all receivers 112 (i.e., 112-1, 112-2, and 112-3).

A drawback of the combinatorial-type of arrangement is that for a delivery system having n reservoirs (for I ingredients, where I≦n) and m receivers, n×m valves are required. For example, a system having five reservoirs and sixteen receivers requires eighty valves, which is an expensive proposition. Furthermore, the large number of valves can cause reliability issues—a problem with any one of the eighty valves will require shutdown of the system. Furthermore, the large number of intermediate valves and fluidic channels increases the likelihood of cross-contamination (e.g., due to inadequate cleaning between uses, etc.), precipitation of solids within the valves and channels, and other problems.

So, a problem presents itself. When creating mixtures in which all ingredients must be combined at substantially the same time, or in which multiple copies of the mixture or variations of it must be created at the substantially the same time, how can the equipment-intensive arrangements of the prior art be avoided?

SUMMARY OF THE INVENTION

A HTE-capable delivery system and method for combining ingredients that solves the problem that is posed above and that avoids some of the drawbacks of the prior art is disclosed.

In accordance with the invention, and unlike prior-art combinatorial-type systems, ingredients are delivered in pulses to receivers. Each pulse contains only a minor portion of the total amount of ingredient to be dispensed. In the illustrative embodiment, ingredients are delivered individually (not pre-mixed with any other ingredient), although this is not a requirement of the method or the system.

In some embodiments, the pulses are sequenced so that each ingredient is added to all the receivers in a very short period of time. As a consequence of this sequencing:

any one ingredient is added to all of the receivers at nearly the same time;

when multiple ingredients are added to a receiver, they are added at nearly the same time;

mixtures formed in each receiver are formed at about the same time; and successive drops of a particular ingredient are dispensed into a particular receiver at nearly the same time.

This provides a capability of forming mixtures for which all ingredients must be added at nearly the same time. And because the dispensing operation is pulsed and sequenced, the dispensing system that is used to dispense the ingredients can have conduits that do not directly couple to a receiver (unlike prior-art combinatorial-type delivery systems; see FIG. 1). A system in accordance with the illustrative embodiment of the present invention can, therefore, be substantially less equipment intensive than prior-art combinatorial-type delivery systems.

In particular, some variations of the illustrative system have only one dispensing element (e.g., valve, nozzle, orifice, tube, etc.) per ingredient dispensed, irrespective of the number of receivers in the system. Consequently, a five-reservoir dispenser in accordance with the illustrative embodiment that dispenses into sixteen receivers uses only five dispensing elements, as compared to eighty for some prior-art arrangements.

An ancillary benefit of pulsed dispensing is that since each pulse of ingredient delivered to a receiver contains substantial kinetic energy, some degree of mixing occurs without using an external mixer.

In some embodiments of a delivery system in accordance with the illustrative embodiment of the present invention, the dispensing elements are moved into aligned with the receivers to dispense ingredients. Delivery systems having dispensing elements that move to receivers, or receivers that move to dispensing elements are known in the art. In operation, these prior-art dispensers are typically operated to deliver a full charge of liquid ingredient to a first receiver vessel, and then fill others vessels, seriatim. But, as a consequence of their programming and other limitations, these dispensers cannot be used for applications wherein multiple ingredients, which cannot be pre-mixed with one another, are added to a plurality of receivers at nearly the same time, and with adjustable ratio control of ingredient flow.

The incremental, pulse-wise addition of ingredients described herein is performed in such a way that, from the "perspective" of the mixture being formed, the ingredients are added quasi-continuously or quasi-simultaneously or both. These terms have a particular meaning for use in this specification, and are explicitly defined in the "Detailed Description" section below. But by way of introduction, the term "quasi-continuous" means that the addition of an ingredient to a receiver is considered to be substantially continuous from the "perspective" of the mixture being formed. And one meaning of the term "quasi-simultaneous" is that all ingredients are added to a receiver at substantially the same time from the "perspective" of the mixture being formed. The significance of the phrase "from the perspective of the mixture" is that the actual addition of ingredient can be rapid or slow, as a function of the nature of the mixture.

A delivery system in accordance with the invention includes a system controller, a drive system and a dispensing system. Using information about the drive system, the dispensing system, the receivers, and the mixture being formed, the system controller is capable of:
  determining an execution sequence in accordance with a dispensing protocol;
  causing the drive system to align, on an ongoing basis, the dispensing system and the receivers in accordance with the execution sequence; and
  causing the dispensing system to dispense ingredients into each of the receivers in accordance with the execution sequence.

The dispensing protocol dictates that:
  ingredients are dispensed in a plurality of pulses, wherein each pulse contains a minor fraction of the total quantity of ingredient to be dispensed within a selected time interval; and
  dispensing is quasi-continuous; or
  dispensing is quasi-simultaneous; or
  dispensing is quasi-continuous and quasi-simultaneous.

In some embodiments, determining the execution sequence comprises:
  determining the speed (which can be varied during the operation) at which the dispensing system and receivers are moved relative to one another (although in other embodiments, the relative movement is intermittent);
  determining the quantity of ingredient delivered during each pulse (which can be varied during the operation), per ingredient, per receiver; and
  determining the time sequencing of pulses, per ingredient.

In some embodiments, when the proportions of the various ingredients that compose a mixture are similar (e.g., 1:1.1:0.9:1.2:1, etc.), a small amount of each ingredient will typically be dispensed into a given receiver before that receiver gets "seconds" of any particular ingredient. After all the receivers receive a small amount of each ingredient (via a pulse from each dispensing element), a first dispensing cycle is completed. A second cycle then follows without interruption, wherein each of the receivers gets a second pulse of one or more of the ingredients.

When there are substantial imbalances in the proportions of the various ingredients that compose the mixture (e.g., 1:1:1:1:0001, etc.), it might be advantageous not to deliver minor ingredients in some dispensing cycles because of the difficulty of accurately dispensing such small quantities of liquid. As a consequence of skipping cycles, a greater quantity of the ingredient will be dispensed when the pulse occurs. As an alternative, lower flow-rate valves can be used for minor ingredients so that it is not necessary to skip dispensing cycles.

The drive system of the quasi-continuous dispenser can be configured in a variety of ways. For example, in one implementation, the drive system includes a gantry that is rapidly positionable in one or more directions. The gantry positions the dispensing system, which includes one or more dispensing elements, over the receivers. Once positioned, at least one of the dispensing elements in the system dispenses, via a pulse, a small amount of an ingredient into a receiver. The dispensing system is then rapidly repositioned, under the control of the system controller, enabling the same or different ingredients to be dispensed into the same or different receivers. The dispensing operation continues, under the control of the system controller, until the required delivery profile for each ingredient is satisfied.

In another implementation, a rotary drive system is used. The rotary drive system has a higher throughput than a gantry-based drive system and avoids the potentially problematic, rapid, reciprocating motion of the gantry-based drive system. Gantry-type motion results in the "FILO" (First In Last Out) problem, wherein after the last dispense within a cycle, the gantry must be returned to its original position to start a subsequent cycle.

In some embodiments, the rotary drive system includes at least one arm (more typically two to six arms) that is positioned over a plurality of receivers. The arm, which in the illustrative embodiment is capable of being rapidly rotated, advantageously includes at least one dispensing element that dispenses an ingredient into the receivers.

A rotary dispenser that incorporates a rotary drive system and that is suitable for use in conjunction with the present invention is described in applicants' co-pending application entitled "Rotary-Drive Dispenser," filed on even date herewith as Ser. No. 60/441,757 and incorporated by reference herein.

Regardless of dispenser configuration, it is advantageous (but not necessary) to incorporate analytical testing capabilities into the delivery system. Preferably, on-line samples are taken from receivers as the mixtures are being produced. One or more test(s) are performed on the samples using one or more test stations. Test results can then be sent to the system controller to close a control loop. That is, based on the test results, the system controller can modify the dispensing protocol (e.g., amount of ingredient delivered per pulse length, pulse frequency, etc.) as required to keep the mixtures on specification.

To that end, some variations of the illustrative system incorporate an analysis station, such as the analysis station described in the Rotary-Drive Dispenser application referenced above. One of these analysis stations is capable of performing at least one type of analysis on the mixtures being produced in each of the receivers.

Often, the amount of an ingredient that is contained in each dispensing pulse is quite small (typically in the range of nanoliters to microliters). Consequently, the delivery system is advantageously capable of accurately dispensing very small quantities of liquid to avoid inaccuracies in the mixtures. Since most valves have limited life expectancy when dispensing such small liquid quantities (at a high-frequency of operation), it is advantageous to use a valveless dispensing system. Some variations of the illustrative delivery system therefore incorporate a valve-less dispensing element, as can be implemented using a nozzle described in applicant's co-pending application entitled "Rotary-Drive Dispenser," referenced above.

These and other variations of a delivery system and method in accordance with the illustrative embodiment of the present invention are illustrated in the Drawings and described further in the Detailed Description section of this specification.

The following non-limiting example is provided by way of an introduction to the concepts of (1) quasi-continuous dispensing; (2) quasi-simultaneous dispensing; (3) the significance of pulsed delivery of ingredients; and (4) as an example of a use for the illustrative method and delivery system.

EXAMPLE I

Four ingredients are to be delivered from a delivery system having four dispensing elements, one ingredient from each dispensing element. The ingredients are to be delivered to four receivers to create four identical mixtures. The receivers are aligned in a circular pattern. The dispensing elements are moved along a circular path over the receivers. The delivery system delivers ingredients via pulses into the receivers. A pulse lasts for 0.025 seconds, and, at any given moment, a different ingredient is delivered into each of the four receivers. The dispensing elements are being moved at a rate of one revolution per 0.5 seconds (i.e., in one revolution, each dispensing element passes over all four receivers).

In operation, in the first 0.025 seconds, one pulse of ingredient is dispensed into each receiver, with a different ingredient being dispensed into each receiver. For example, a pulse of ingredient "A" is dispensed into receiver "1," a pulse of ingredient "B" is dispensed into receiver "2," and so forth. The full pulse is delivered to each receiver before the dispensing element is out of dispensing range of that receiver. As each element passes into range of the next receiver, a second pulse of ingredient is delivered, one ingredient per receiver. So, after these two pulses, each receiver contains one pulse of each of two ingredients. For example, one pulse of ingredient "A" and one pulse of ingredient "D" has been added to receiver "1" and one pulse of ingredient "B" and one pulse of ingredient "A" has been added to receiver "2."

Pulsed dispensing continues. After one complete revolution, each receiver contains one pulse of each of the four ingredients. The time elapsed is 0.5 seconds. Thus, in 0.5 seconds, any given receiver contains a small quantity of each of the four ingredients ("the mixture"), and each receiver contains the same small amount of the mixture. These are both attributes of what is meant by "quasi-simultaneous" dispensing.

Soon after completing the first revolution, each dispensing element is in range to deliver a second pulse of an ingredient to the receiver into which they first dispensed that ingredient. Thus, the second pulse of ingredient "A" is delivered to receiver "1," the second pulse of ingredient "B" is delivered to receiver "2," and so forth. Since the first cycle was completed after 0.5 seconds, the second pulse of each ingredient is delivered by 0.5025 seconds. The rate, in this case a relatively rapid rate, at which successive pulses of an ingredient are received by a particular receiver is an attribute of "quasi-continuous" dispensing. That is, with a particular ingredient being dispensed into a particular receiver at a rate of one pulse each 0.5 seconds, the dispensing is nearly continuous or "quasi" continuous.

It is to be understood that this Example is provided by way of introduction to the concepts of quasi-continuous dispensing and quasi-simultaneous dispensing, as described herein, and should not be considered as a limitation on the application of these concepts. In particular, an important aspect of these concepts is that they are defined relative to a mixture being created. That is, as a function of the properties of the ingredients and the mixture, quasi-continuous dispensing and quasi-simultaneous dispensing can correspond to a very slow actual rate of dispensing of ingredients into receivers.

Also, in Example I, the length of each pulse (and hence the amount of ingredient delivered) is assumed to be invariant from pulse to pulse and to be the same for each ingredient. But as desired, the length of a pulse can be varied from pulse-to-pulse and from ingredient-to-ingredient.

Furthermore, in many applications, the composition of the mixtures being formed will vary from one receiver to the next (e.g., by changing the amount of one ingredient, etc.), rather than being identical as in the Example. Also, in some embodiments, more than one pulse of an ingredient is delivered to a particular receiver before any pulses of that ingredient are received by any of the other receivers. Further, the timing between pulses can vary.

These and other variations on the concepts of quasi-continuous dispensing and quasi-simultaneous dispensing, and their application to the creation of mixtures, will be described later in this specification.

BRIEF DESCRIPTION OF THE DRAWINGS

FIG. 7 depicts a block-flow diagram of a method for producing a mixture in accordance with the illustrative embodiment of the present invention.

FIG. 8 depicts a dispensing system with a gantry drive with x-axis and y-axis positioning for use in conjunction with the illustrative embodiment of the present invention.

FIG. 9 depicts a dispensing system with a rotary drive for use in conjunction with the illustrative embodiment of the present invention.

FIG. 16 depicts a third illustrative addition profile for three ingredients, which are being dispensed into each of three receivers, in accordance with the protocols and methods described herein.

DETAILED DESCRIPTION

Figure 1:
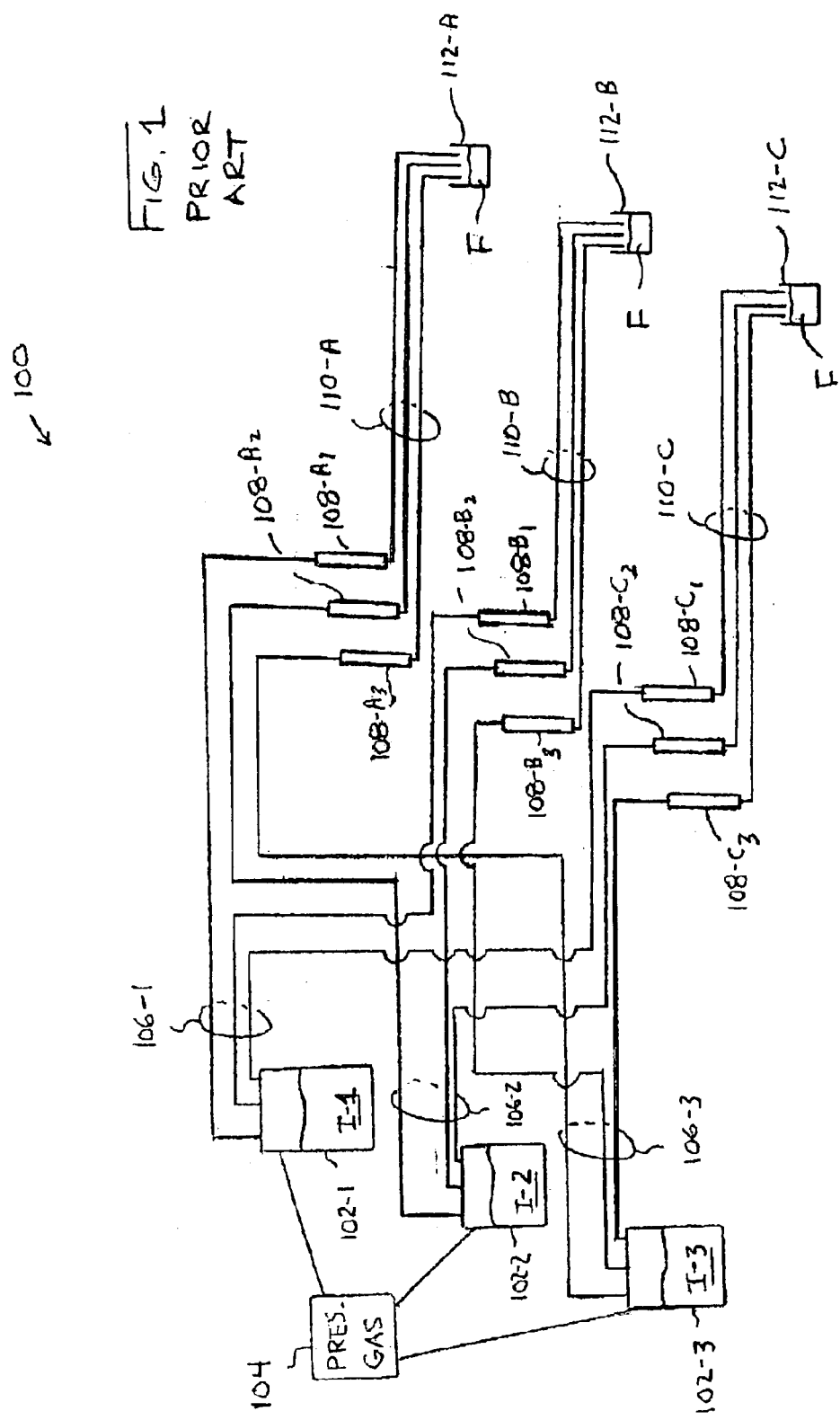
FIG. 1 depicts a prior-art HTE-capable delivery system.

Definition of terms and additional considerations:

"Liquid(s)" means material(s) that are liquid at the temperature of the dispensing process, materials that are liquefied by various physical processes, liquid suspensions (e.g., material(s) that are suspended in a liquid carrier, etc.), slurries, even solids that have properties that allow them to "flow," (e.g., fluidized solids, etc.). Thus, the term "liquid" includes solids that are "naturally" flowable or rendered flowable using appropriate operations (e.g., processing, etc.) or appropriate conditions (e.g., temperature, etc.), etc.

"Fluid" means gases, vapors, and liquids.

"Coupled" means that (coupled) elements cooperate, communicate, attach to, or otherwise influence or affect one another. For example, fluid can flow between coupled elements (e.g., a reservoir and a dispensing element coupled by a conduit, etc.). Also, a force exerted by or experienced by a first of two coupled elements can affect the second element, whether or not the two elements are directly attached to one another.

Tasks and Subtasks. The operation of the illustrative method is described in terms of tasks and subtasks, rather than steps. This is because, as will be clear to those skilled in the art, some of the described tasks and subtasks can be performed in a single step, while others cannot. Furthermore, the illustrative embodiment is more easily understood when it is described in terms of its constituent tasks and subtasks than if it were described, formalistically, in terms of "steps."

Elements described in terms of their function. Some elements of the illustrative apparatus are described functionally, or in terms of the tasks or subtask that they carry out. As will be clear to those skilled in the art, these elements can be implemented using shared or dedicated hardware including, for example, hardware capable of executing software, such as a suitably-programmed, general purpose processor.

Additional definitions are provided throughout the specification.

The illustrative embodiment of the present invention provides an HTE-capable method and apparatus for producing mixtures of ingredients (e.g., formulations, etc.) according to a specific profile of addition. In some versions of the illustrative method, a plurality of ingredients is added to a plurality of receivers in such a way that the addition of ingredients is considered to be "quasi-continuous" or "quasi-simultaneous" or both. To implement quasi-continuous dispensing or quasi-simultaneous dispensing with dispensers having conduits that do not directly couple each ingredient to a receiver, the ingredients are delivered in increments—in pulses.

As used in this specification, the term "quasi-continuous" means that the addition of an ingredient to a receiver is considered to be substantially continuous from the "perspective" of the mixture being formed.

In some cases of quasi-continuous dispensing, the actual pace of incremental addition of ingredient is so rapid that the ingredient appears to flow almost continuously into a receiver. In some other cases, however, the actual pace of addition is not rapid, and is more properly characterized as "slow." In these latter cases, the pace of addition is considered to be quasi-continuous in the sense that the mixture being formed is insensitive (e.g., there are no deleterious affects on the mixture, etc.) to the actual time interval between successive dispenses. It is understood that for some mixtures, this interval of insensitivity is measured in fractions of a second, while for others it is measured in hours or even days. Both these scenarios (i.e., rapid-in-fact addition and slow-in-fact addition) are examples of quasi-continuous dispensing, as that term is used herein.

Furthermore, in some versions of the illustrative method, the addition of ingredients into the plurality of receivers is considered to be "quasi-simultaneous." As used in this specification, the term "quasi-simultaneous" means that:

(1) all ingredients are added to a given receiver at substantially the same time; or (2) a given ingredient is added to successive receivers at substantially the same time; or (3) all ingredients are added to all receivers at substantially the same time; or (4) any combination thereof.

The word "simultaneous," as it appears in the definition given by provisoes (1) through (4), is referenced to the mixture being formed. More particularly, given various mixtures that have a limited tolerance to sequential addition of ingredients, there will be some variation as to how long the absence of an ingredient can be tolerated without affecting the mixture (e.g., causing undesirable side reactions, etc.) In some cases, the addition of one or more ingredients, as per provisoes 1–4, is nearly simultaneous-in-fact. That is, ingredients are added at such a rapid pace that it appears as if each of the ingredients is being added simultaneously to the one or more receivers. This might be required to due intolerance for delay, or due to a desire to rapidly produce mixtures, or for other reasons.

In some other cases, there is a substantial time delay between the introduction of different ingredients into a single receiver, or between the introduction of the same ingredient into different receivers. This delay is permissible only in cases in which the mixture being formed is insensitive to such delays—this is what is meant by the word "simultaneous" being referenced to the mixture being formed. Both of these scenarios are examples of quasi-simultaneous dispensing, as that term is used herein.

Dispensing ingredients as a plurality of pulses in repetitive fashion, in accordance with the quasi-continuous and quasi-simultaneous delivery protocols described herein, enables ingredient-delivery profiles that could not be achieved, at least without substantial inconvenience, using other approaches. "Quasi-continuous" delivery and "quasi-simultaneous" delivery of ingredients are illustrated by the following two examples, which are simplified, relative to an actual dispensing scenario, for pedagogical purposes. The examples below illustrate "rapid-in-fact" addition of ingredient(s).

EXAMPLE II

Consider a system wherein a single ingredient, which is being dispensed from a single dispensing element, is delivered to eight receivers in pulse-wise fashion in accordance with the illustrative embodiment of the invention. A total amount of ingredient to be dispensed to each receiver is 10 milliliters ("ml") over a ten-minute period, corresponding to a continuous introduction rate of 1 ml per minute or $\frac{1}{60}$ ml per second. Based on the nature of the ingredient, it is determined that successive pulses of liquid into a given receiver must occur in one second or less.

Assume that the ingredient is to be dispensed every $\frac{1}{8}$ second, and that a dispenser (and drive system) that is capable of doing this is available. To achieve the desired rate of addition, each pulse of ingredient contains 16.7 microliters ("$\mu l$") of the ingredient (i.e., 0.167 volume percent of the total amount of ingredient to be delivered to a single receiver, and 0.021 volume percent of the total amount of ingredient to be delivered to all receivers).

Within 1 second, each of the eight receivers receives one pulse—16.7 $\mu l$—of the ingredient, completing a dispensing cycle. After 600 of such cycles, which takes 600 seconds, the required 10 ml of ingredient are delivered to each receiver.

Thus, successive pulses of the ingredient are delivered to any given receiver in one second (while pulses received by neighboring receivers are separated by $\frac{1}{8}$ second). In this example, the delivery of an ingredient every one second to a particular receiver satisfies the definition of "quasi-continuous" dispensing. It is understood that greater elapsed times, e.g., 5 seconds or more, might satisfy the requirement for "quasi-continuous" delivery in other applications with different ingredients.

EXAMPLE III

To illustrate the meaning of "quasi-simultaneous," consider a further example with the same specifications as the last one except that instead of one ingredient, there are five ingredients being dispensed from five dispensing elements. Assume that each dispensing element dispenses an ingredient, pulse-wise, at the same time as every other dispensing element. Also, due to the nature of the ingredients, all ingredients must be delivered to a given receiver within one second ("requirement 1"). Furthermore, due to the experiments being conducted, the mixture being created in each receiver must be formed at substantially the same time ("requirement 2"). These two requirements must be satisfied, for the purpose of this Example, for the dispensing operation to be considered "quasi-simultaneous." It will be understood that in other situations, additional or fewer requirements might need to be met to satisfy the quasi-simultaneous dispensing protocol.

Based on the execution sequence, within 1 second, each of the eight receivers receives five pulses—one pulse of each ingredient, completing a dispensing cycle. After 600 cycles, which again takes 600 seconds, each receiver contains 50 ml of a mixture containing equal amounts of the five ingredients.

Thus, within one second, any given receiver has received one pulse of each of the five ingredients, satisfying requirement 1. And, within one second, all receivers have received a pulse of each of the five ingredients, satisfying requirement 2. Consequently, the requirements for quasi-simultaneous dispensing are satisfied. This Example also satisfies the proviso given in Example 1 for quasi-continuous dispensing. That is, within an elapsed time of one second, successive pulses of an ingredient are received by a receiver.

In view of the foregoing description and definitions, it will be appreciated that the terms "quasi-continuous" and "quasi-simultaneous" are not readily amenable to numerical quantification. Likewise, the amount of ingredient contained in a "pulse" is application dependent. But to provide some context, the following guidelines are offered.

As a function of the nature of the ingredients and the specific application, the elapsed time for successive pulses of ingredient into a receiver (i.e., quasi-continuous dispensing) and the elapsed time for any of the definitions of quasi-simultaneous dispensing (i.e., provisoes 1–4) will fall into one of the following ranges:

- $\leq 0.1$ seconds ("intolerant"); or $\leq 0.5$ seconds ("intolerant"); or $\leq 1.0$ seconds ("intolerant"); or $\leq 5.0$ seconds ("substantially intolerant");
- or $\leq 100.0$ seconds ("somewhat intolerant"); or $\leq 24$ hours ("very tolerant"); or >24 hours ("insensitive").

To create mixtures that are intolerant of delays (i.e., $\leq 0.1$ seconds; or $\leq 0.5$ seconds; or $\leq 1.0$ seconds), a rotary-drive dispenser, such as is described in applicant's "Rotary-Drive Dispenser" patent application, is likely to be required. To create mixtures that are "substantially intolerant" to delays (i.e., $\leq 5.0$ seconds), then either a rotary-drive dispenser or a gantry-type dispenser can suitably be used.

The dispensing protocols described herein—that is: pulsed, quasi-continuous, and quasi-simultaneous delivery—are most critical for mixtures that are "intolerant" or "substantially intolerant" of delays. And when using delivery systems other than the combinatorial-type described in the Background section, the dispensing protocols described herein might be the only way to create these mixtures.

These protocols are also useful in conjunction with mixtures that are "somewhat intolerant," "very tolerant," and "insensitive" to delays. But the application of the protocols to these types of mixtures is far less critical in being able to create the mixture in an efficient, cost-effective manner. For example, when elapsed time is restricted to 100 seconds or less, a rotary-drive dispenser, gantry-type dispenser, and perhaps other types of dispensers can suitably be used. And when the allowed elapsed time is 24 hours or less, or more than 24 hours, then virtually any type of dispenser can be used.

With regard to the quantity of ingredient "contained" within a pulse, in most cases, pulses will contain no more than 20 percent of the total amount of an ingredient to be dispensed to a receiver. Usually, pulses will contain a far smaller percentage; such as between about $4 \times 10^{-5}$ volume percent to about 1.0 volume percent of the total amount of an ingredient to be dispensed to a receiver. In terms of absolute volume, the amount of liquid contained in a pulse will typically fall within a range of about 2 nanoliters to 1 milliliter.

So, as a consequence of dispensing ingredients in accordance with the pulsed, quasi-continuous and quasi-simultaneous protocols described herein, problems that might otherwise arise when ingredients are added in sequential fashion (i.e., all of ingredient one, then all of ingredient two, and so forth) are avoided.

The illustrative method and apparatus are particularly useful for applications in polymer chemistry, in particular polymers produced by a living polymerization, crosslinked polymers, photocured and photolytically cross-linked polymers, in the continuous creation of compositionally-varying fibers, tapes, and film, among others. It will be understood, however, that the illustrative method and apparatus are suitable for dispensing many different types of ingredients to produce many different types of mixtures. Examples include personal-care products (e.g., shampoo, perfume, etc.), household cleaning products ((e.g., liquid dishwashing detergents and clothes-cleaning detergents, etc.), foods, industrial products (e.g., engine oil, lubricants, industrial cleaners, etc.), adhesives (e.g., glues, resins, etc.), paints and coatings, pharmaceutical products, and electronics "chemicals" (e.g., solder masks, etch resist masks, etc.), to name but a few. The ingredients are advantageously liquid, or otherwise liquefied, so that they flow under appropriate conditions.

Having described the concept of pulsed, quasi-continuous, and quasi-simultaneous simultaneous dispensing, a description of a system and method for implementing the protocols are now described.

Figure 2:
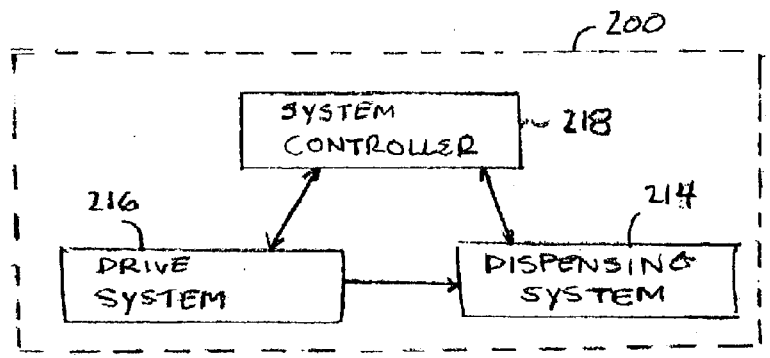
FIG. 2 depicts a block diagram of an HTE-capable delivery system in accordance with the illustrative embodiment of the present invention.

FIG. 2 depicts a block diagram of system 200 in accordance with the illustrative embodiment of the present invention. System 200 includes system controller 218, drive system 216 and dispensing system 214, interrelated as shown.

Dispensing system 214 includes a plurality of dispensing elements (see, e.g., FIGS. 8 and 9) for dispensing fluid, which is typically liquid. Dispensing system 214 will usually have two to six dispensing elements, although fewer or more can suitably be used as is appropriate for the needs of a particular application. For many uses, each dispensing element will dispense a different ingredient. Although in some applications, it might be advantageous for the same ingredient to be dispensed from two dispensing elements (e.g., when an ingredient is a major component of a mixture such that it must be dispensed at a substantially greater rate than other ingredients, etc.).

Dispensing system 214 dispenses the ingredients into a plurality of receivers. The particular type of receiver (e.g., microtitre plates, vials, etc.) that is selected depends, to a certain extent, upon the particulars of dispensing system 214. That is, dispensing system 214 can be implemented in a variety of ways, and for some implementations, microtitre plates can be used, whereas for others, they cannot. Several specific embodiments of dispensing system 214 are described later in this specification.

As described further below, responsive to system controller 218, drive system 216 causes a relative movement between the dispensing elements of dispensing system 214 and the receivers. This relative movement enables the ingredients to be dispensed, on an on-going basis, into an appropriate receiver at an appropriate time to create a desired mixture.

Several specific embodiments of drive system 216 and dispensing system 214 are described later in this specification. In the illustrative embodiments, drive system 216 causes the dispensing-elements of dispensing system 214 to move to the receivers. In other embodiments (not depicted, see, e.g., applicant's co-pending patent application "Rotary-Drive Dispenser," previously referenced), drive system 216 moves the receivers to the dispensing elements. In still other embodiments, it is possible to use rotary (multi-port) valves to distribute ingredients. But rotary-valve-based dispensers that are suitable for implementing the protocols described herein are expected to be less preferred than rotary-drive or gantry based dispensers due to reliability and maintenance issues. It is inconsequential, in terms of implementing the principles of the present invention, whether drive system 216 moves the dispensing elements to the receivers or moves the receivers to the dispensing elements, or, in alternative embodiments, whether a multi-port valve or other mechanism is used.

System controller 218 directs the operation of dispensing system 214 and drive system 216. More particularly, system controller 218 performs the following tasks, in addition to any others:

determines an execution sequence based on a dispensing protocol;

causes drive system 216 to align, on an ongoing basis, the dispensing elements of dispensing system 214 and the receivers in accordance with the execution sequence; and causes dispensing system 214 to dispense ingredients into the appropriate receivers in accordance with the execution sequence.

These tasks are described below with reference to FIGS. 3–7.

Figure 3:
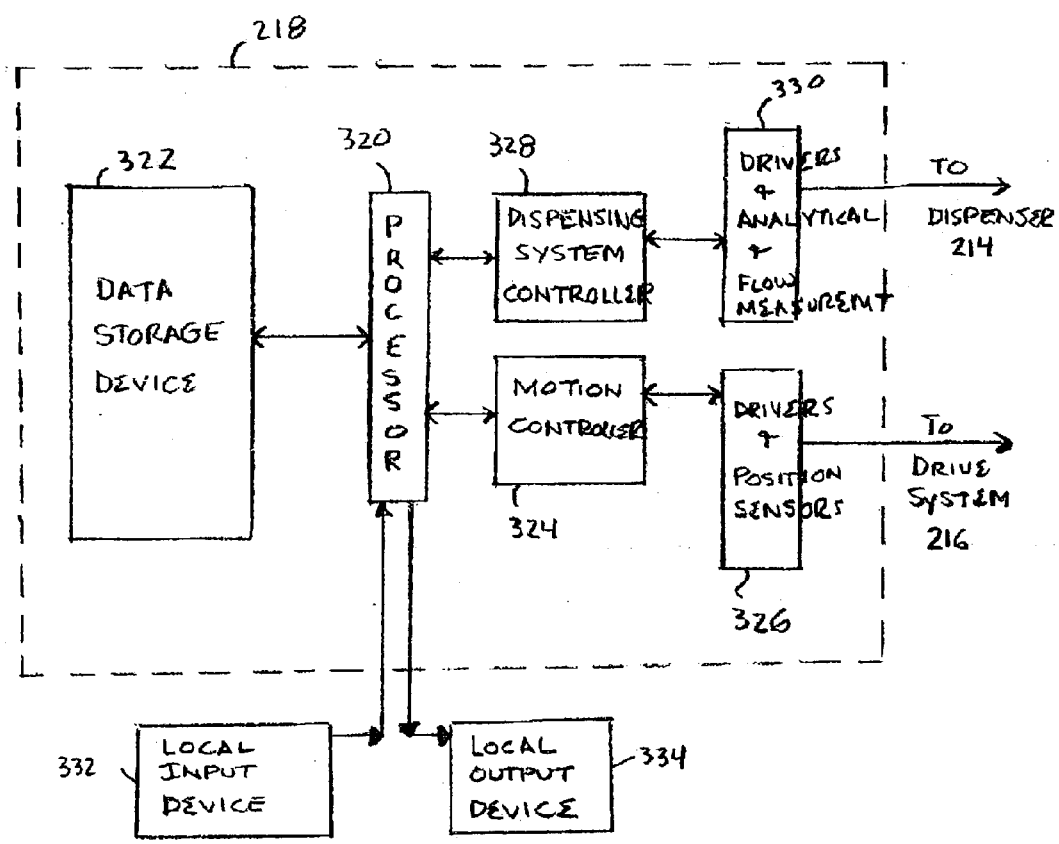
FIG. 3 depicts a block diagram of a system controller for use in the system of FIG. 2.

FIG. 3 depicts a block diagram of the salient components of system controller 218. As will be understood by those skilled in the art, most of the components that compose system controller 218 are implemented using shared or dedicated hardware including, for example, hardware capable of executing software, such as a suitably-programmed, general-purpose processor, etc.

In the embodiment depicted in FIG. 3, system controller 218 includes processor 320, data storage device 322, motion controller 324, motion drivers and position sensors 326, dispensing-system controller 328, dispensing-system drivers, analytical, and flow measurement 330, interrelated as shown.

Figure 6:
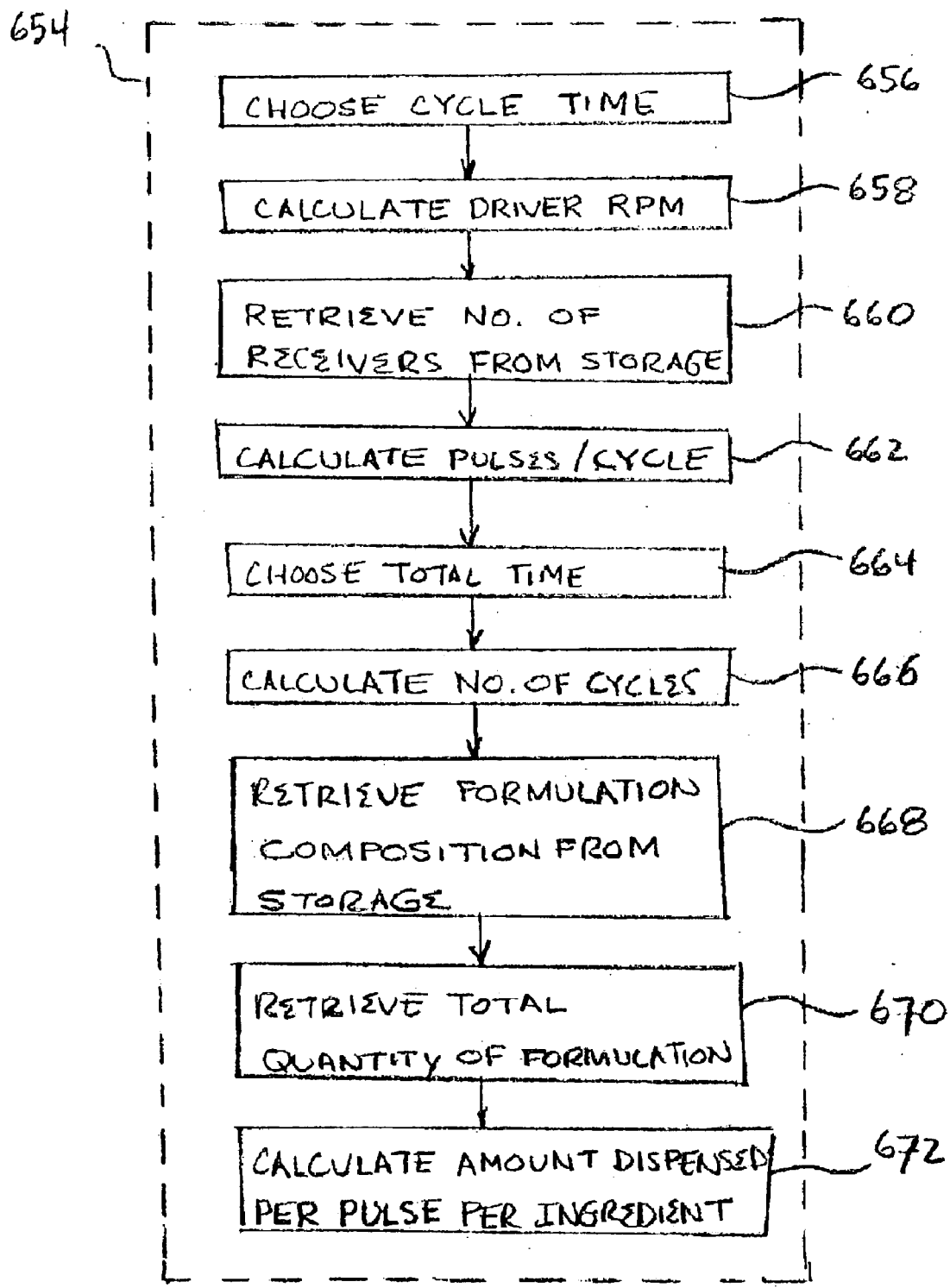
FIG. 6 depicts a block-flow diagram of a method for completing a task carried out by the system controller.

Processor 320 is a special or general-purpose processor that is capable of performing the tasks described below. In particular, and without limitation, processor 320 is capable of:

receiving data from a local input device 332 (e.g., keyboard, etc.) and outputting it to a local output device 334 (e.g., monitor, etc.);

storing parameters that are required to determine the execution sequence (see, e.g., FIGS. 5 and 6) and retrieving those parameters from data storage device 322;

executing one or more software programs that are stored in data storage device 322, including a program for determining the execution sequence (see FIG. 6);

storing the execution sequence in data storage device 322 (see FIG. 4); and controlling the operation of motion controller 324 and dispensing-system controller 328 (thereby controlling the dispensing operation) in accordance with the execution sequence.

Data storage device 322 is a non-volatile memory (e.g., an EEPROM, a tape drive, disk drives, an optical device, etc.) for storing programs that are executed by processor 320, physical properties/pressure/flow data for use with the programs, and data that is input into and generated by processor 320, among other information.

Motion controller 324 converts commands (e.g., move at a speed dictated by the execution sequence, etc.) that are issued by processor 320 into actuator (motor) control instructions. In conjunction with motion drivers/position sensors 326, motion controller 324 generates relative movement between dispensing system 214 and receivers. As previously indicated, in the embodiments described herein, motion controller moves the dispensing elements of dispensing system 214 to align them, on a continuing basis, with the receivers. Position sensors 326 provide positional information (absolute or relative) to motion controller 324 so that it "knows" the position of dispensing system 214 (i.e., the position of the dispensing elements) relative to the receivers at all times.

Dispensing-system controller 328 converts commands (e.g., dispense at times dictated by the execution sequence, etc.) that are issued by processor 320 into actuator (flow) control instructions. In conjunction with dispensing-system drivers/analytical & flow measurement 330, dispensing-system controller 328 causes dispensing system 214 to dispense ingredients. Optional flow measurement data and optional analytical measurement data can be obtained from appropriate devices and used to close a control loop (e.g., flow rate, mixture composition, etc.).

It will be appreciated that the specifics of motion drivers/position sensors 326 and dispensing-system drivers/analytical & flow measurement 330 depend upon dispensing system 214 and drive system 216 configuration. Those skilled in the art will know how to design and implement these components.

As previously indicated, one of the tasks of system controller 218, and more particularly processor 320, is to determine an execution sequence that is based on a defined dispensing protocol. The execution sequence, and the dispensing protocol on which it is based, are key aspects of the present invention. It is by operating dispensing system 214 and drive system 216 in accordance with the execution sequence that ingredients are dispensed quasi-continuously or quasi-simultaneously or both. Of course, the execution sequence is of no use unless it is coupled with a dispensing system and a drive system that are capable of executing it (such as dispensing system 214 and drive system 216).

Based on the dispensing protocol, and certain input parameters (described later), the execution sequence is determined. The execution sequence specifies, among any other parameters:

the speed or speed profile (the speed can vary) at which the dispensing elements move relative to the receivers (e.g., rpm, etc.) or vice versa;

the quantity of ingredient dispensed per pulse per ingredient per receiver (which can vary from pulse-to-pulse, ingredient-to-ingredient and receiver-to-receiver);

the time sequencing of pulses, per ingredient.

Illustrative system 200 is advantageously suitable for operating under these constraints. Elapsed times (for successive pulses of an ingredient into a receiver, or for any of the definitions of quasi-simultaneous) of less than 1 second can, in fact, be achieved with illustrative system 200, as configured with a rotary-drive dispenser, such as is described later in this specification and in the pending "Rotary-Drive Dispenser" application that was previously referenced. It will be clear that system 200 is also capable of operating with relatively slower pulse and sequencing times.

Figure 4:
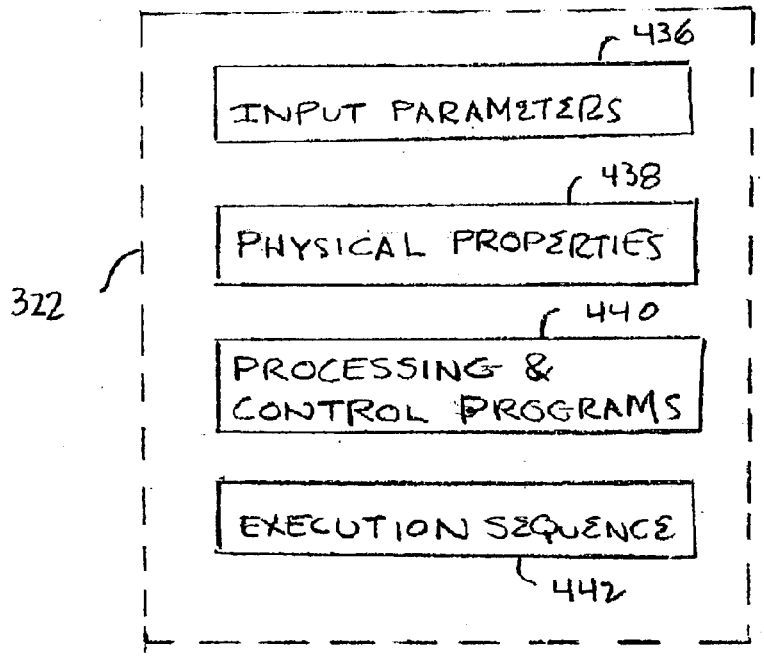
FIG. 4 depicts a block diagram of some of the contents of a data storage device for use in the system controller of FIG. 3.
Figure 5:
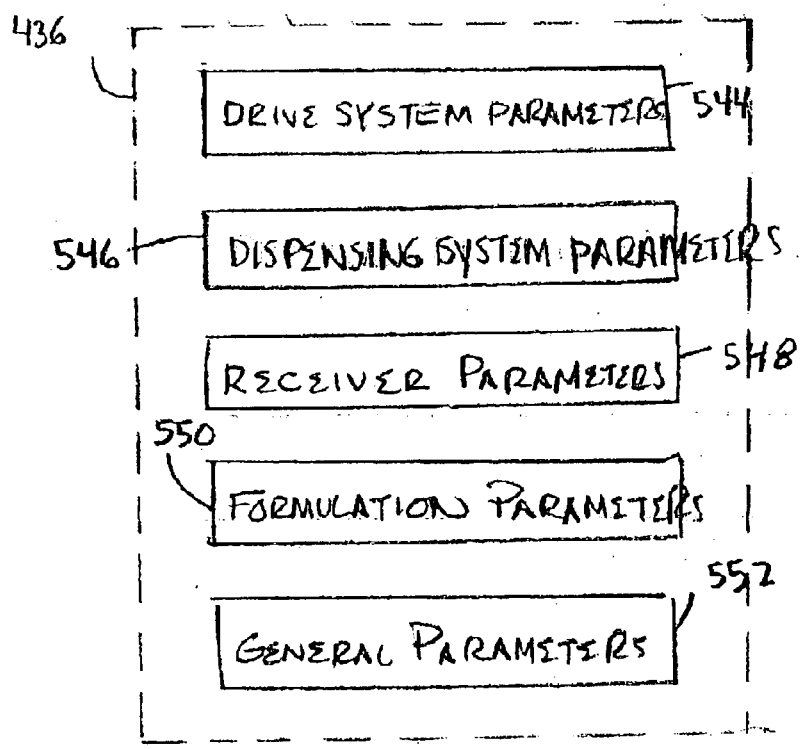
FIG. 5 depicts a block diagram of some of the contents of a data item in the data storage device of FIG. 4.

In the illustrative embodiment, the execution sequence is determined via processor 320 running appropriate software and using appropriate input parameters and other data. FIGS. 4 through 6 depict further detail of elements of system controller 218 that are germane to an understanding of the present invention and, in particular, to the task of determining the execution sequence.

FIG. 4 depicts, via a block diagram, some of the content of data storage device 322. Some of the content depicted in FIG. 4 is accessed by processor 320 to determine the execution sequence. The depicted content includes input parameters 436, flow characteristics and physical properties 438, and processing & control programs 440. This content can be configured for storage and access in a variety of ways known to those skilled in the art (e.g., look-up tables, etc.).

The content labeled "Input Parameters 436" includes information that is used by the relevant Processing & Control Program 440 to determine the execution sequence. As indicated in FIG. 5, this information can be sub-divided into several groupings, including "Drive-System Parameters" 544, "Dispensing-System Parameters" 546, "Receiver Parameters" 548, "Mixture Parameters" 550 and "General Parameters" 552.

Drive-System Parameters 544 includes information about drive system 216 (e.g., x, y, x-y, x-z, y-z, or x-y-z gantry-type, rotary, or other types, limitations on rate of movement, etc.). Dispensing-System Parameters 546 include information about dispensing system 214 (e.g., number of dispensing elements, minimum quantity of ingredient that can be dispensed by the dispensing elements, the range of dispensing pressure, etc.). Since, for a given system 200, drive system 216 and dispensing system 214 will not change, Drive-System Parameters 544 and Dispensing-System Parameters 546 are typically input into data storage device 322 once when the system is commissioned.

Receiver Parameters 548 includes information about the receivers, such as the number of receivers being used, the volume of the receivers, their positions, etc. Mixture Parameters 550 include information about the mixture to be produced, such as the number of ingredients, the viscosity of the ingredients, the relative amount of each ingredient in the mixture, whether or not it is acceptable to pre-mix any of the ingredients and, if so, which ones, etc.

General Parameters 552 includes information about the total quantity of mixture being produced per receiver, the maximum allowable time for producing the mixture, the maximum allowable time between successive pulses, etc.

With reference to FIG. 4, Physical Properties 438 includes information that is used by the relevant Processing & Control Programs 440 to assist in implementing the execution sequence. For example, after a "quantity dispensed per pulse per ingredient per receiver" is determined as part of the execution sequence, information concerning the relationship between ingredient viscosity vs. pressure vs. flow for the dispensing elements must be accessed to ensure the proper amount of ingredient is dispensed per pulse. Such information is typically input into data storage device 322 only once when the system is commissioned.

Processing & Control Programs 440 includes programs that are run by the processor, such as, for example, the program that determines the execution sequence. Execution Sequence data item 442 is an updateable data file in which the execution sequence is stored once it is determined by processor 320.

As previously described, the execution sequence specifies the speed or speed profile at which the dispensing elements move relative to the receivers (e.g., rpm, etc.), the quantity of ingredient dispensed per pulse per ingredient per receiver, and the sequencing of pulses, per ingredient. It is to be understood that one or more of these parameters determined by the execution sequence can change during the course of a dispensing operation. Such change can be pre-determined, or occur in response to feedback concerning the dispensing operation.

A variety of different methods or algorithms can be used to determine the execution sequence. In particular, some algorithms determine a "workable" but "arbitrary" execution sequence. That is, such an execution sequence is determined without regard to its performance relative to other possible execution sequences. Alternatively, some other algorithms determine an "efficient" execution sequence. As to the determination of efficient execution sequences, several approaches can be adopted. In a "brute-force" approach, a number of candidate execution sequences are determined and then a most efficient execution sequence is selected from among the candidates based on a comparison of certain parameters (e.g., total time for creating the formulation, minimum mechanical movement, etc.). Alternately, the algorithm itself can be "efficient," employing various techniques (e.g., intelligent pruning, etc.) for determining an efficient execution sequence. Those skilled in the art will be able to develop and implement algorithms for determining the execution sequence.

By way of example, FIG. 6 depicts a block flow diagram of algorithm 654 for determining an execution sequence. Algorithm 654 is for use with a rotary-driven system and in the specific instance of a constant rotational speed. An algorithm for determining an execution sequence for discontinuous rotational movement or changeable speed, or for a gantry-driven system would be somewhat different. It is within the capabilities of those skilled in the art to develop algorithms for use with either type of drive system and for various types of operation.

Algorithm 654 is simplified for pedagogical purposes; that is, it is provided to illustrate basic calculations that are performed in the course of determining an execution sequence. After the subtasks that compose algorithm 654 are described, various complexities that are advantageously handled by such an algorithm are described. It is to be understood that, for the most part, there is no significance to the order in which the various subtasks composing algorithm 654 are performed. That is, the illustrative order is arbitrary and the subtasks can be sequenced in a different order.

At subtask 656, a cycle time is chosen. The cycle time is the time that it takes for all dispensing elements to dispense a pulse of an ingredient into all receivers (for this simple case of equal-time pulses for each ingredient and for constant speed, etc.). This time can be based on reactivity considerations of the ingredients, productivity considerations, or other factors.

In subtask 658, the speed at which the dispensing elements must be moved is calculated based on the chosen cycle time. As an Example, assume that a cycle time of 1 second is chosen. For a cycle time of 1 second, the dispensing elements move at 1 revolution per second or 60 rpm.

In subtask 660, the number of receivers (in which the mixture is being produced) is retrieved from data storage device 322. A pulse rate is determined, in subtask 662, by dividing the cycle time by the number of receivers. Assuming that there are 12 receivers, the pulse rate is twelve pulses per second (so that each of the twelve receivers receives a "pulse" of an ingredient in a cycle). Although as described later in this specification, the pulse rate might be changed as a result of considerations related to the composition of the mixture.

In subtask 664, a total time for producing the mixture is chosen. This time might be dictated by the reactivity of the mixture or by any of a number of other considerations. Based on the total time, and knowing the cycle time, the total number of dispensing cycles is calculated in subtask 666. For example, assuming that the mixture is to be produced in 30 minutes, and assuming a cycle time of 1 second, the number of cycles is: 30 minutes×60 seconds per minute×1 cycle per second=1800 cycles.

In subtask 668, the composition of the mixture is retrieved from data storage device 322. The composition information might show, for example, that ingredient "A" is 15 volume percent ("vol. %") of the mixture, ingredient "B" is 22 vol. %, ingredient "C" is 17 vol. %, ingredient "D" is 25 vol. %, and ingredient "E" is 21 vol. %. In subtask 670, the total quantity of mixture being produced in the receivers is retrieved from data storage device 322.

TABLE I

Amount Dispensed per Pulse per Ingredient

| IN-GRE-DIENT | PROPORTION OF INGREDIENTS <Vol %> | TOTAL AMOUNT DISPENSED <ml> | AMT. DISPENSED PER CYCLE <µl> | AMT. DISPENSED PER PULSE <µl> |
|---|---|---|---|---|
| A | 15 | 7.5 | 4.2 | 0.35 |
| B | 22 | 11.0 | 6.1 | 0.51 |
| C | 17 | 8.5 | 4.7 | 0.39 |
| D | 25 | 12.5 | 6.9 | 0.58 |
| E | 21 | 10.5 | 5.8 | 0.48 |
| Total | 100 | 50.0 | 26.7 | |

Based on the information retrieved in subtasks 668 and 670, the amount dispensed per pulse per ingredient (and per receiver) is calculated in subtask 672. Based on the compositional breakdown provided above, and assuming that 50 ml of the mixture is being produced, the amount dispensed per pulse per ingredient (per receiver) is given in Table I above.

So, for the parameters provided above, the execution sequence, as determined by algorithm 654, is:

a dispensing element speed of 60 rpm;

the quantity of ingredient dispensed per ingredient per pulse (per receiver) is as given above; and the sequencing of pulses per ingredient is 12 per second.

As indicated above, algorithm 654 is simplistic. One aspect of this simplicity is that the execution sequence determined by algorithm 654 provides multiple versions of the same mixture produced with the same addition profile. In other words, for any given ingredient, the amount that is dispensed to each receiver is the same. By way of illustration, for ingredient A in the example above, a pulse containing 0.35 µL is delivered to each of the twelve receivers.

In some cases, multiple identical copies of a mixture are desired; in many other cases, however, it will be desirable to vary each of the mixtures, such as, for example, by changing the amount of one or more of the ingredients from receiver to receiver. The algorithm for determining the execution sequence advantageously provides this capability. In operation, this change in the quantity dispensed per pulse can be implemented by changing flow rate (i.e., by changing dispensing pressure or orifice size), or by changing the length (time) of the pulse (i.e., the amount of time the dispensing element is open for dispensing).

For the execution sequence determined by algorithm 654, the dispensing frequency per ingredient is one per ingredient per receiver per cycle. This is acceptable when each of the ingredients of a mixture is present in about the same proportions. But in some mixtures, one or two of the ingredients might be present in very minor amounts compared to the other ingredients. In such a case, the amount of the minor ingredients that must be dispensed per pulse might be too low for accurate dispensing. Consequently, it can be advantageous to dispense minor ingredients every other cycle, etc., so that there will be more (2×) of the ingredient to dispense. The algorithm for determining the execution sequence advantageously provides this capability. Alternatively, a dispensing element that is designed to handle a lower flow rate can be used.

On the other hand, if one ingredient is present at a far greater concentration than other ingredients, it might be advantageous to dispense that ingredient from two (or more) of the dispensing elements. The algorithm for determining the execution sequence advantageously provides this capability.

The algorithm for determining the execution sequence will advantageously check to ensure that calculated values are within the capabilities of the drive and dispensing systems. For example, the algorithm advantageously determines if the value for the amount dispensed per pulse per ingredient is within the limitations of the equipment. If not, the algorithm should be able to adjust variables (e.g., cycle time, total time, total volume of the mixture, etc.) in attempt to provide a workable execution sequence or, alternatively, request operator clarification.

Those skilled in the art will be capable of developing an algorithm for determining an execution sequence that accounts for all such complexities.

It will be understood by those skilled in the art that system controller 218 can be organized differently than depicted in FIG. 3. For example, one alternative is to consider one or more of motion controller 324, motion drivers 326, dispensing system controller 328, and dispensing system drivers 330 to be a part of dispensing system 214, rather than system controller 218. And those skilled in the art will recognize that other alternatives exist as well. Consequently, it is instructive to also define or describe system controller 218 in terms of its function. System controller 218 can be described or defined functionally as including:

means for causing dispensing system 214 to dispense ingredients in a plurality of pulses in accordance with the execution sequence (or means for incrementally dispensing ingredients to receivers via a plurality of pulses); and means for causing dispensing system 214, in conjunction with drive system 216, to dispense ingredients quasi-continuously, quasi-simultaneously, or both.

With reference to the illustrative embodiment depicted in FIG. 3, means for causing dispensing system to dispense (or means for incrementally dispensing) includes: data storage device 322, processor 320 dispensing-system controller 328 and dispenser drivers 330. Means for causing dispensing system, in conjunction with drive system, to dispense quasi-continuously, quasi-simultaneously, or both includes: data storage device 322, processor 320 motion controller 324, motion drivers 326, dispensing-system controller 328 and dispenser drivers 330.

Both of these "means" elements include "means for determining an execution sequence," which, with reference to FIG. 3, includes data storage device 322 and processor 320. And means for determining an execution sequence can be defined as including: means for determining a quantity dispensed in each pulse for each ingredient for each receiver and means for determining a time sequence by which ingredients are dispensed into each receiver.

Again, the association of the components depicted in FIG. 3 with the "means" elements is for pedagogical purposes. Those skilled in the art will recognize that in variations of the illustrative embodiment, the means elements described above can be associated with only some of the components listed above.

FIG. 7 depicts method 700 for producing mixtures in accordance with the illustrative embodiment. In accordance with method 700, task 702 requires determining an execution sequence for dispensing ingredients based on a dispensing protocol. The dispensing protocol has already been described at length. Task 702 comprises the sub-tasks of running an algorithm suitable for determining an execution sequence, such as algorithm 654, and storing the resulting execution sequence in data storage device 322.

As per task 704, ingredients are dispensed in accordance with the execution sequence. As will be appreciated by those skilled in the art, this task comprises sub-tasks involving motion controller 324, motion drivers and position sensors 326, dispensing system controllers 328 and dispensing system drivers 330.

Having described the operation of system controller 218, various implementations of it, and the manner in which it interacts with dispensing system 214 and drive system 216, several specific embodiments of dispensing system 214 and drive system 216 are now described.

Gantry-drive Dispenser

FIG. 8 depicts the salient features of a first embodiment of dispensing system 214 and drive system 216. In this embodiment, the dispensing system is driven by a gantry system that provides x-axis, or x-y axis (and optionally z-axis) positioning. It will be understood that the dispensing and drive systems depicted in FIG. 8 are provided by way of illustration, not limitation; in other embodiments, drive systems with x-axis, or x-y axis positioning, and dispensing systems for use therewith, are configured differently in known fashion to provide the requisite functionality.

The embodiment of dispensing system 214 depicted in FIG. 8 includes environmental enclosure 874, dispensing head 876, housing 878, reservoirs 880A, 880B, and 880C (generally "reservoirs 880,") conduits 882A, 882B, and 882C (generally "conduits 882,") dispensing elements 884A, 884B, and 884C (generally "dispensing elements 884,") and heating blocks 886A and 886B, interrelated as shown.

Dispensing head 876 has housing 878, which receives reservoirs 880. The reservoirs are coupled to dispensing elements 884 by conduits 882. The illustrative embodiment depicted in FIG. 8 shows a 1:1:1 ratio among the number of reservoirs 880, conduits 882, and dispensing elements 884. In some other embodiments, different ratios can be used. For example, in some embodiments, there are a greater number of reservoirs 880 than dispensing elements 884, wherein multiple reservoirs feed a single dispensing element (subject to limitations of cross-contamination and incompatibility of ingredients). In yet further variations, a single reservoir provides ingredient to multiple dispensing elements 884.

Furthermore, while the embodiment depicted in FIG. 8 shows three reservoirs 880, three conduits 882, and three dispensing elements 884, in some other embodiments, more reservoirs, more conduits and more dispensing elements are present. And, of course, it is possible to use fewer reservoirs 880, fewer conduits 882, and fewer dispensing elements 884. In most embodiments, the number of reservoirs 880, conduits 882, and dispensing elements 884 will be in a range of between two to six. The upper limit is constrained by the ability of the dispensing system 214 and drive system 216 to deliver ingredients in accordance with the execution sequence.

Reservoirs 880 are advantageously pressurized by connection to a source of pressurized gas (not shown). Alternatively, reservoirs 880 can be pressurized by gravity feed, positive displacement, etc. In response to commands from system controller 218 (and more particularly from dispensing system controller 328 and drivers 330), dispensing elements 884 deliver ingredients, one pulse at a time, into receivers 898 in receiver plates 896A and 896B consistent with the execution sequence.

Environmental enclosure 874 isolates dispensing head 876 and receiver plates 896A and 896B from the ambient environment. Heating blocks 886A and 886B provide heat to receivers 898 as might be required.

Drive system 216 moves dispensing head 876 and dispensing elements 884 so that ingredients are delivered to different receivers 898. The execution sequence advantageously avoids FILO, trying to maintain a repeatable sequence (requiring an extra return motion). The embodiment of drive system 216 depicted in FIG. 8 includes two linear drive systems, which are (arbitrarily) defined as an "x-axis drive system" and a "y-axis drive system." As used herein, the term "linear drive system" means a mechanism capable of moving an object in linear motion.

The x-axis and y-axis drives are conventional mechanisms that include a drive means, and a guide along which an object is moved. For example, in the illustrative embodiments, the drives are implemented as a stepper motor that drives a ball-screw assembly. In particular, x-axis drive system includes x-axis stepper motor 888 and x-axis, ball-screw assembly 890. The y-axis drive system includes y-axis ball-screw assemblies 894A, 894B, and 894C (collectively "y-axis ball screw assemblies 894,") and three y-axis stepper motors (not shown) that are disposed within housing 878. The stepper motors are available from any of a number of suppliers, such as Applied Motion Products of Watsonville, Calif. The ball-screw assemblies are available from any of a number of suppliers, such as NSK Corporation of Schaumberg, Ill.

Dispensing head 876 is movable in a lateral direction (i.e., to the "left" and to the "right" in FIG. 8) along ball-screw assembly 890 by x-axis stepper motor 888. The stepper motor operates in response to commands from system controller 218 (and more particularly from motion controller 324 and drivers 326 ) consistent with the execution sequence. This lateral movement serves to align dispensing elements 884 with various receivers 898 in a given row (i.e., along the x direction) in receiver plates 896A and 896B.

Dispensing elements 884 are movable by ball-screw assemblies 894 along a direction that is orthogonal (i.e., "out-of-the-page" in FIG. 8) to the direction of movement of dispensing head 876. Ball-screw assemblies 894 move under the control of the y-axis stepper motors in response to commands from system controller 888. This movement serves to align dispensing elements 884 with various receivers 898 in parallel columns (i.e., along the y direction) in receivers plates 896A and 896B. The dispensing elements are individually positionable along the y-direction.

An advantage of gantry-drive dispensers is that the x, x-y, and x-y-z positioning elements are commercially available from any of a variety of suppliers (e.g., Tecan, CCS Packard, Metler-Toledo, etc.). ps Rotary-drive Dispenser FIG. 9 depicts the salient features of a second embodiment of dispensing system 214 and drive system 216. In this embodiment, the dispensing system is driven in rotary motion by drive system 216. The rotary-drive system and dispensing system summarized below is more fully described in applicant's co-pending application for a "Rotary-Drive Dispenser," previously referenced. It will be understood that the dispensing and drive systems depicted in FIG. 9 are provided by way of illustration, not limitation; in other embodiments, rotary-drive dispensing systems having different configurations from the system depicted in FIG. 9 (e.g., rotating receivers 942 rather than rotating dispensing elements 912, etc.) and that provide the required functionality can suitably be used in conjunction with the present invention.

With reference to FIG. 9, dispensing system 214 includes reservoir(s) 928-1 and 928-2 (generally "reservoir(s)" 928 ), liquid-transport arrangement(s) 930-1 and 930-2 (generally, "liquid-transport arrangement(s) 930"), dispensing element (s) 912-1 and 912-2 (generally "dispensing element(s) 912"), and receiver support platform 916.

Reservoirs 928 store the ingredients that are to be dispensed by dispensing elements 912. The ingredients are advantageously stored in liquid form in the reservoirs. In the illustrative embodiment, each reservoir 928 is fluidically coupled to a respective dispensing element 912 via a respective liquid-transport arrangement 930. In the illustrative embodiment, liquid-transport arrangement 930-1 comprises conduit 932-1 (and a check valve, which is not shown), positive-displacement pump 934-1 and conduit 936-1. Likewise, liquid-transport arrangement 930-2 comprises conduit 932-2 (and a check valve, which is not shown), positive-displacement pump 934-2 and conduit 936-2. In some other liquid-transport arrangements 130 suitable for use in conjunction with the present invention, pump 934 is not used; rather, reservoirs 928 are pressurized, such via connection to a source of pressurized gas. In yet some other liquid-transport arrangements, a gravity-induced flow is used. In some additional liquid-transport arrangements 930 that are suitable for use in conjunction with the present invention, neither a pump nor a source of pressurized gas to pressurize reservoirs 928 is used. Rather, low pressure is developed in dispensing elements 912, wherein the low pressure draws liquid ingredient from reservoirs 928.

With respect to liquid-transport arrangement 930-1, pump 934-1 takes suction from the reservoir 928-1. When actuated by dispensing system controller 328 and drivers 330 (see, FIG. 3), pump 934-1 draws in liquid ingredient 938-1 from the reservoir through conduit 932-1 and pumps it through conduit 936-1 to dispensing element(s) 912-1. Dispensing element 912-1 then dispenses liquid ingredients 938-1 into an underlying receiver 942. Liquid-transport system 930-2 functions in the same fashion in conjunction with reservoir 928-2 and dispensing element 912-2.

Receiver support platform 916 is sandwiched between rotatable member 902 (described below) and reservoir support platform 924 (described below). Platform 916 "surrounds" drive shaft 914, but is not coupled to it. In other words, platform 916 is not driven by drive shaft 914; rather, drive shaft 914 simply passes through centrally-located opening 918 in platform 916. Upper surface 920 of platform 916 receives one or more receivers 942-1 (generally, "receivers 942") at near-perimeter region 922 (only one receiver 942-1 is shown in FIG. 9 for the sake of clarity). The radial position of dispensing elements 912 (on arms 904 of rotatable member 902 ) is such that dispensing elements 912 overlie near-perimeter region 922. Therefore, to the extent that an arm 904 is angularly aligned with a receiver 942, the dispensing element 912 that depends from that arm will overlie that receiver.

Drive system 216 includes drive 903, drive shaft 914, reservoir support platform 924, and rotatable member 902. In the embodiment depicted in FIG. 9, rotatable member 902 has two arms 904-1 and 904-2 (generally "arm(s) 904"). Rotatable member 902 is coupled, near its mid-point 906, to drive shaft 914. Dispensing element 912-1 depends from arm 904-1 near end 908 and dispensing element 912-2 depends from arm 904-2 near end 910.

Reservoir support platform 924 is located beneath receiver support platform 916. Upper surface 926 of reservoir support platform 924 receives one or more reservoirs 928. Two of these reservoirs (i.e., reservoirs 928-1 and 928-2 ) are depicted in FIG. 9. Like rotatable member 902, reservoir support platform 924 is rotatably coupled to drive shaft 914.

Rotatable member 902 can have fewer or more arms 904 than the two that are depicted in FIG. 9. It has been indicated elsewhere in this specification that it is advantageous, in some applications, to have five, six or some other number of dispensing elements. Consequently, it will be advantageous, in some embodiments, to have five, six or some other number of arms 904.

In operation, arms 904 move in rotary fashion at a rate dictated by the execution sequence. (The rate can be varied. Also, the motion can be continuous or intermittent.) Drive shaft 914 is coupled to drive 903, which is disposed within base 940. When actuated by motion controller 324 and drivers 326 (see,. FIG. 3), drive 903 (e.g., a motor, turbine, etc.), which is coupled to drive 903, rotates drive shaft 914, such as in the direction indicated by arrow 944. Drive shaft 914, in turn, drives both rotatable member 902 and second platform 924 in the same direction. The rotatable member and second platform are advantageously driven at the same rate. This ensures that conduits 936 will not twist and fail, as would otherwise occur if there were a relative rotational motion between rotatable member 902 and second platform 924.

Rotation of rotatable member 902 brings dispensing elements 912 into alignment with successive underlying receivers 942-1, etc. At the appropriate time, as dictated by the execution sequence and in response to the action of dispensing system controller 328 and drivers 330, liquid-delivery arrangement(s) 130 and dispensing element(s) 112 deliver successive pulses of ingredient to receivers 942.

In accordance with the illustrative embodiment, platform 916 is not coupled to drive shaft 914. Nevertheless, platform 916 is advantageously (but not necessarily) rotatable, as indicated by arrows 946 and 948. To the extent that platform 916 is rotatable, it is advantageously driven by its own drive system (not depicted) so that it rotates independently of rotatable member 902. A reason for providing this independent rotational capability is so that this embodiment of dispensing system 214 and drive system 216 can be used with an analytical station. In other variations of the drive system/dispensing system that is depicted in FIG. 9, platform 916 is not rotatable, or is otherwise not suitable for use in conjunction with the subject analytical station. While such other variations of a rotary dispenser cannot be used with the analytical station described in applicant's co-pending patent application entitled "Rotary-Drive Dispenser," they can be used to implement a dispensing protocol in accordance with the present invention. In other words, the compositional or other data provided by such an analytical station is not required to implement the dispensing protocol described herein.

As previously indicated, it is to be understood that the function of drive system 216 is to create a relative motion between dispensing elements 912 and receivers 942. In the illustrative embodiment, this relative motion is created by moving dispensing elements 912 while receivers 942 are kept stationary. In some other embodiments (not shown) however, dispensing elements 912 are stationary while receivers 942 are moved. A rotary-drive dispenser that is configured in this fashion is suitable for conducting quasi-continuous dispensing and quasi-simultaneous dispensing as described herein.

Example IV below provides an illustration of how the rotary-drive dispenser depicted in FIG. 9 can be used to produce a plurality of mixtures in accordance with the dispensing protocol described herein.

EXAMPLE IV

For this Example, the rotary-drive dispenser includes six reservoirs 928-1 through 928-6 and rotatable member 902 having six arms 904-1 through 904-6 and six dispensing elements 912. Only five of the reservoirs (i.e., reservoirs 928-1, 928-2 and 928-4 through 928-6 ) are dispensing respective ingredients A, B, C, D, and E through five dispensing elements (i.e., dispensing elements 912-1, 912-2 and 912-4 through 912-6 ). Ingredients are to be dispensed into eight receivers 942-1 through 942-8. See, FIG. 10. The cycle time (i.e., the time it takes for all the receivers to receive a small amount of each of the formulation ingredients via a "pulse" from each dispensing element) is 0.8 seconds. Each of the eight receivers receives the same amount—10 milliliters—of ingredients B, C, D, and E; however, the amount of ingredient A that is dispensed to each of receivers 942-1 through 942-8 is varied. In particular, while receiver 942-1 receives a total of 10 ml of ingredient A, the other receivers receive a reduced amount as follows (in milliliters):

| Receiver: | 942-1 | 942-2 | 942-3 | 942-4 | 942-5 | 942-6 | 942-7 | 942-8 |
|---|---|---|---|---|---|---|---|---|
| Quantity: | 10.0 | 9.8 | 9.5 | 9.2 | 9.0 | 8.8 | 8.6 | 8.4 |

In some embodiments, the deficit in total liquid volume that results from the reduction in an ingredient (e.g., ingredient A, etc.) can be compensated for by the addition of an appropriate amount of an inert liquid compound. Alternatively, if the difference in total volume of the various mixtures is relatively small, then it is preferable not to add any diluent to compensate for lost volume. Such decisions are best made on a case-by-case basis by those skilled in the art. For the present example, no additional liquid is added.

The addition profile specifies uniform introduction of ingredients in the appropriate proportions over a thirty-minute period. Since each dispensing cycle takes 0.8 seconds, a total of: (30×60) seconds×1 cycle per 0.8 seconds=2250 cycles are required.

Assuming that ingredients B, C, D, and E are dispensed in equal (quantity) pulses, each pulse of ingredients B, C, D, and E contains: 10 ml /2250 cycles=4.44 micro-liters of liquid.

As to ingredient A, the quantity of liquid in the pulses varies as a function of which receiver receives the ingredient. Assuming that 2250 equal pulses are delivered to any given receiver, the pulses contain the following quantities (in micro-liters) of ingredient A:

| Receiver: | 942-1 | 942-2 | 942-3 | 942-4 | 942-5 | 942-6 | 942-7 | 942-8 |
|---|---|---|---|---|---|---|---|---|
| Quantity: | 4.44 | 4.36 | 4.22 | 4.09 | 4.00 | 3.91 | 3.82 | 3.73 |

Tables II, III and IV below show the first, second and final dispensing cycles, respectively, for this Example. Tables III into receiver 942-7, and 4.44 micro-liters of ingredient E has been dispensed into receiver 942-8. During this first pulse, no ingredients are dispensed into receivers 942-2, 942-4, and 942-6, since no dispensing element 912 was near to receivers 942-2 and 942-6 and dispensing element 912-3, which is aligned with 942-2, is not dispensing any ingredient for this particular formulation.

At 0.1 seconds, the second pulse-begins. By the time the second pulse begins, the rotatable member 902 has rotated counterclockwise. Dispensing element 912-1 is now in position to dispense ingredient A into receiver 942-2, and so forth. Only 4.36 micro-liters of ingredient A are delivered to receiver 942-2.

TABLE II

First Dispensing Cycle — Quantity of Ingredient Dispensed ($\mu l$)

Figure 10:
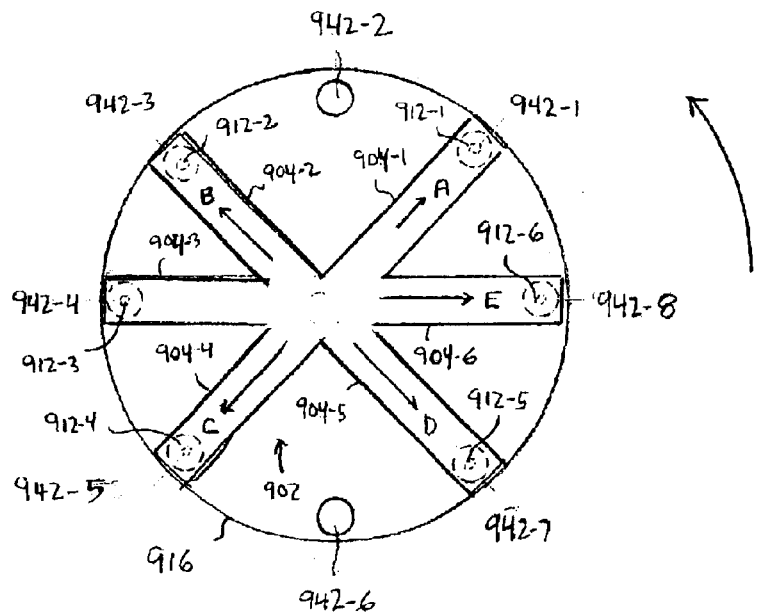
FIG. 10 depicts a top view of a rotary-drive dispensing system and provides a "snap shot" of the dispenser as each cycle begins.

| TIME, sec<br>RECEIVER | 0.0<br>1ST PULSE | 0.1<br>2ND PULSE | 0.2<br>3RD PULSE | 0.3<br>4TH PULSE | 0.4<br>5TH PULSE | 0.5<br>6TH PULSE | 0.6<br>7TH PULSE | 0.7<br>8TH PULSE |
|---|---|---|---|---|---|---|---|---|
| 942-1 | 4.44A | 4.44E | 4.44D | — | 4.44C | — | 4.44B | — |
| 942-2 | — | 4.36A | 4.44E | 4.44D | — | 4.44C | — | 4.44B |
| 942-3 | 4.44B | — | 4.22A | 4.44E | 4.44D | — | 4.44C | — |
| 942-4 | — | 4.44B | — | 4.09A | 4.44E | 4.44D | — | 4.44C |
| 942-5 | 4.44C | — | 4.44B | — | 4.00A | 4.44E | 4.44D | — |
| 942-6 | — | 4.44C | — | 4.44B | — | 3.91A | 4.44E | 4.44D |
| 942-7 | 4.44D | — | 4.44C | — | 4.44B | — | 3.82A | 4.44E |
| 942-8 | 4.44E | 4.44D | — | 4.44C | — | 4.44B | — | 3.73A | and IV show cumulative ingredient dispensed. FIG. 10 is a "snap shot" of the rotary-drive dispenser (top view) as each cycle begins ($1^{st}$ pulse), wherein:

dispensing element 912-1 dispenses ingredient A into receiver 942-1;

dispensing element 912-2 dispenses Ingredient B into receiver 942-3;

dispensing element 912-3 does not dispense (into receiver 942-4 );

dispensing element 912-4 dispenses ingredient C into receiver 942-5;

dispensing element 912-5 dispenses ingredient D into receiver 942-7; and dispensing element 912-6 dispenses ingredient E into receiver 942-8.

With reference to Table II and FIG. 10, after the first pulse of the first cycle has occurred, 4.44 micro-liters of ingredient A has been dispensed into receiver 942-1, 4.44 micro-liters of ingredient B has been dispensed into receiver 942-3, 4.44 micro-liters of ingredient C has been dispensed into receiver 942-5, 4.44 micro-liters of ingredient D has been dispensed In this Example, rotatable element 902 is in constant motion. That is, dispensing elements 912 are not simply positioned over a receiver 942 and then the ingredients are dispensed; rather, the ingredients are dispensed "on-the-fly" (i.e., while rotatable element 902 is in motion). Thus, operation of the dispensing system 214 and drive system 216 must be well synchronized, which is the responsibility of system controller 218.

After the eighth pulse of the first cycle, 4.44 micro-liters of ingredients B, C, D, and E have been delivered to each of receivers 942-1 through 942-8. And an amount of ingredient A between 4.44 micro-liters (into receiver 942-1 ) and 3.73 micro-liters (into receiver 942-8 ) is dispensed into the receivers 942 in accordance with the execution sequence.

By the end of the seventh pulse (elapsed time of 0.7 seconds), a first pulse of all ingredients A through E are received, for example, by receiver 942-1. This illustrates "quasi-simultaneous" dispensing in accordance with the dispensing protocol. At 0.9 seconds, the first pulse of the second cycle begins, such that about 0.8 seconds elapses between successive deliveries of ingredient A into receiver 942-1. This illustrates "quasi-continuous" dispensing.

TABLE III

Second Dispensing Cycle — Cumulative Ingredient Dispensed ($\mu l$)

| TIME, sec<br>RECEIVER | 0.8<br>1ST PULSE | 0.9<br>2ND PULSE | 1.0<br>3RD PULSE | 1.1<br>4TH PULSE | 1.2<br>5TH PULSE | 1.3<br>6TH PULSE | 1.4<br>7TH PULSE | 1.5<br>8TH PULSE |
|---|---|---|---|---|---|---|---|---|
| 942-1 | 8.88A | 8.88E | 8.88D | — | 8.88C | — | 8.88B | — |
| 942-2 | — | 8.72A | 8.88E | 8.88D | — | 8.88C | — | 8.88B |
| 942-3 | 8.88B | — | 8.44A | 8.88E | 8.88D | — | 8.88C | — |
| 942-4 | — | 8.88B | — | 8.18A | 8.88E | 8.88D | — | 8.88C |
| 942-5 | 8.88C | — | 8.88B | — | 8.00A | 8.88E | 8.88D | — |

TABLE III-continued

| Second Dispensing Cycle — Cumulative Ingredient Dispensed (µl) | | | | | | | | |
|---|---|---|---|---|---|---|---|---|
| TIME, sec | 0.8 | 0.9 | 1.0 | 1.1 | 1.2 | 1.3 | 1.4 | 1.5 |
| RECEIVER | 1ST PULSE | 2ND PULSE | 3RD PULSE | 4TH PULSE | 5TH PULSE | 6TH PULSE | 7TH PULSE | 8TH PULSE |
| 942-6 | — | 8.88C | — | 8.88B | — | 7.82A | 8.88E | 8.88D |
| 942-7 | 8.88D | — | 8.88C | — | 8.88B | — | 7.64A | 8.88E |
| 942-8 | 8.88E | 8.88D | — | 8.88C | — | 8.88B | — | 7.46A |

Table III records, on a pulse-by-pulse basis, the accumulation of ingredients in each of receivers 942-1 through 942-8 for the second dispensing cycle.

TABLE IV

| Final Dispensing Cycle — Cumulative Ingredient Dispensed (ml) | | | | | | | | |
|---|---|---|---|---|---|---|---|---|
| TIME, sec | 1799.2 | 1799.3 | 1799.4 | 1799.5 | 1799.6 | 1799.7 | 1799.8 | 1799.9 |
| RECEIVER | 1ST PULSE | 2ND PULSE | 3RD PULSE | 4TH PULSE | 5TH PULSE | 6TH PULSE | 7TH PULSE | 8TH PULSE |
| 942-1 | 10.0A | 10.0E | 10.0D | — | 10.0C | — | 10.0B | — |
| 942-2 | — | 9.8A | 10.0E | 10.0D | — | 10.0C | — | 10.0B |
| 942-3 | 10.0B | — | 9.5A | 10.0E | 10.0D | — | 10.0C | — |
| 942-4 | — | 10.0B | — | 9.2A | 10.0E | 10.0D | — | 10.0C |
| 942-5 | 10.0C | — | 10.0B | — | 9.0A | 10.0E | 10.0D | — |
| 942-6 | — | 10.0C | — | 10.0B | — | 8.8A | 10.0E | 10.0D |
| 942-7 | 10.0D | — | 10.0C | — | 10.0B | — | 8.6A | 10.0E |
| 942-8 | 10.0E | 10.0D | — | 10.0C | — | 10.0B | — | 8.4A |

Table IV above shows the cumulative results after the final dispensing cycle. After the eighth pulse of the last cycle, 10 millimeters of ingredients B through E has been dispensed into each of the receivers. Ingredient A has been dispensed in an amount between 10 and 8.4 milliliters in accordance with requirements.

It is notable that, in this example, (1) successive pulses of an ingredient are dispensed to different receivers; and (2) successive pulses received by a receiver comprise different ingredients. For example, with regard point 1, the first pulse of ingredient A is delivered to receiver 942-1, the second pulse of ingredient A is delivered to receiver 942-2, the third pulse to receiver 942-3, and so forth. Only after each of the receivers 942 has received a pulse of ingredient A does receiver 942-1 receive a second pulse of ingredient A. And with regard to point 2, the first pulse of ingredient to receiver 942-1 is ingredient A, the second pulse of ingredient into receiver 942-1 is ingredient E, the third pulse of ingredient into receiver 942-1 is ingredient D, and so forth.

In some other embodiments, a pulsed, quasi-continuous, quasi-simultaneous dispensing protocol can be implemented when successive pulses of an ingredient are delivered to the same receiver. But these other embodiments must satisfy the following proviso for at least one ingredient of the mixture. In particular, at least some amount of the ingredient must be delivered to a second receiver before all of the ingredient that is intended for the first receiver is delivered to the first receiver.

Figure 11A:
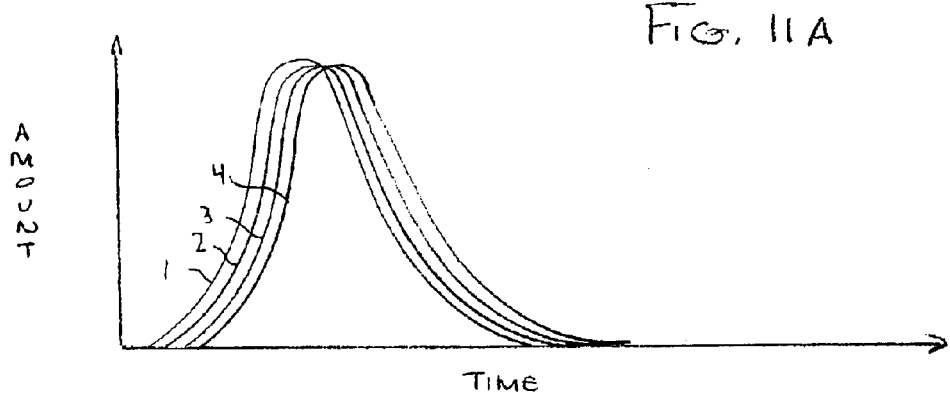
FIGS. 11A and 11B depict a comparison of two ingredient addition profiles in accordance with the illustrative embodiment of the present invention.
Figure 11B:
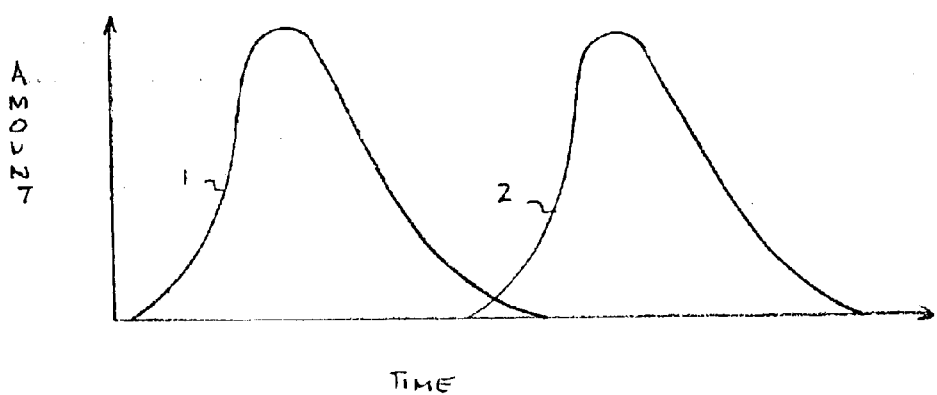

This distinction is depicted graphically in FIGS. 11A and 11B. FIG. 11A depicts the amount 1 of an ingredient that is dispensed to a first receiver, the amount 2 of the ingredient that is dispensed to a second receiver, the amount 3 of the ingredient that is dispensed to a third receiver, and the amount 4 of the ingredient that is dispensed to a fourth receiver. FIG. 11A depicts a scenario in which successive pulses of an ingredient are received by different receivers, such that there is a substantial overlap in terms of the time at which ingredient is dispensed into the various receivers. FIG. 11B depicts a scenario wherein most of the amount 1 of the ingredient that is intended for receiver 1 is delivered to it before a subsequent receiver (i.e., receiver 2) receives any of the ingredient (amount 2).

The methods described herein can be used to create mixtures in accordance with a wide variety of ingredient delivery profiles, a few of which are illustrated via FIGS. 12–16.

Figure 12:
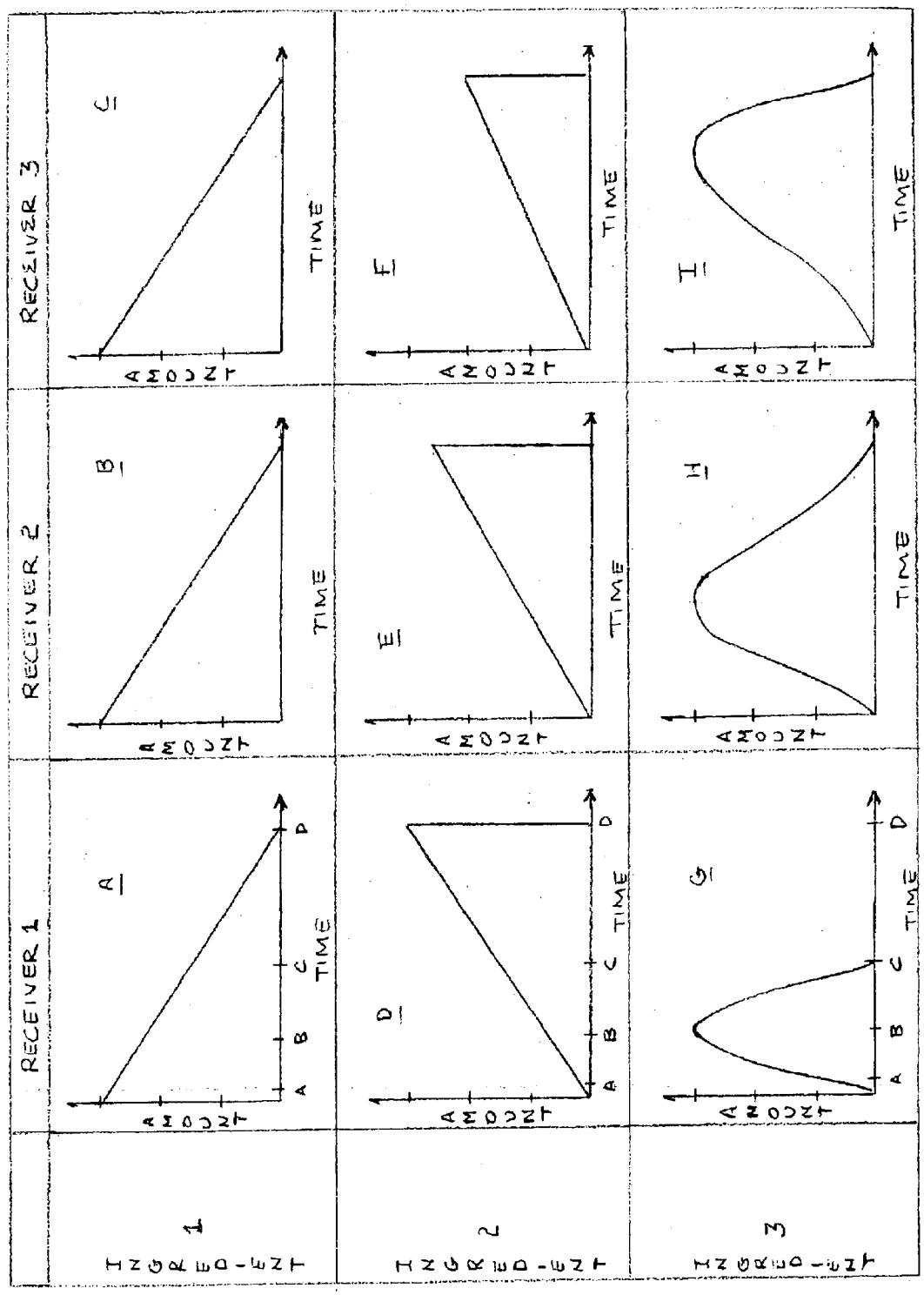
FIG. 12 depicts a first illustrative addition profile for three ingredients, which are be dispensed into each of three receivers, in accordance with the protocols and methods described herein.

FIG. 12 depicts an addition profile for three ingredients, which are being dispensed into each of three receivers. The ingredients are dispensed according to the protocols that are described herein (i.e., in pulses, quasi-continuously and quasi-simultaneously). Whereas in earlier examples, most parameters (e.g., the amount of ingredient dispensed over time, the rate of dispensing, etc.) were held constant, FIG. 12 provides an example wherein a variety of parameters are changing (1) over time; (2) from ingredient-to-ingredient; and (3) from receiver-to-receiver. It is understood that the plots that are shown in FIG. 12 are "smoothed;" ingredients are not dispensed continuously, but rather in pulsed fashion as described herein.

Ingredient 1 (plots A, B, and C) is delivered to each of the receivers at a rate that falls linearly over time. Ingredient 2 (plots D, E, and F) is delivered to each of the receivers at rate that increases linearly over time. Ingredient 3 (plots G, H, and I) is delivered to each of the receivers at a rate that increases, in non-linear fashion, to a maximum, and then decreases in non-linear fashion.

Receiver 1 (Plots A, D, and G)

Ingredients 1 and 2 are dispensed for the same period of time, and Ingredient 3 is dispensed for about half of this time period. The rate of change in amount dispensed of Ingredients 1 and 2 is the same. Ingredients 1 and 2 have the same maximum and minimum dispensing rate. Consequently, equal amounts of Ingredient 1 and 2 are delivered, overall, to Receiver 1.

Only at one point in time is the dispensing rate for Ingredients 1 and 2 the same. For about half of the time, the rate of delivery of Ingredient 1 is greater than the rate of delivery of Ingredient 2. For the other half of the time, the rate of delivery of Ingredient 2 is greater than the rate of delivery of Ingredient 1.

The relative amount of the ingredients being dispensed at any given time changes significantly over time. For example, at time A, substantially more of Ingredient 1 is dispensed than Ingredients 2 and 3, which are dispensed in near-equal quantities. At time B, somewhat more of Ingredient 3 is dispensed than Ingredient 1, and substantially less of Ingredient 2 is dispensed. At time C, equal amounts of Ingredients 1 and 2 are dispensed, and a substantially less of Ingredient 3 is dispensed. At time D, a maximum amount of Ingredient 2 is dispensed, a minimum amount of Ingredient 1 is dispensed, and Ingredient 3 is not dispensed.

Receiver 2 (Plots B, E, and H)

Ingredients 1, 2, and 3 are dispensed for the same amount of time into Receiver 2. The maximum dispensing rate of Ingredient 1 is greater than the maximum dispensing rate of Ingredient 2, and the rate of change in the dispensing rate of Ingredient 1 is greater than the rate of change in the dispensing rate of Ingredient 2. The relative amount of ingredients being dispensed at any given time changes significantly over time, and is different than for Receivers 1 or 3.

Receiver 3 (Plots C, F, and I)

Ingredients 1, 2, and 3 are dispensed for the same amount of time into Receiver 3. The maximum dispensing rate of Ingredient 1 is greater than the maximum dispensing rate of Ingredient 2, and the rate of change in the dispensing rate of Ingredient 1 is greater than the rate of change in the dispensing rate of Ingredient 2. The relative amount of ingredients being dispensed at any given time changes significantly over time, and is different than for Receivers 1 or 2.

Ingredient 1 (Plots A, B, and C)

The addition profile of Ingredient 1 is the same for each receiver.

Ingredient 2 (Plots D, E, and F)

The maximum dispensing rate and the rate of change in dispensing rate decreases from Receiver 1 to Receiver 2 to Receiver 3.

Ingredient 3 (Plots G, H, and I)

Ingredient 3 is dispensed into Receiver 1 for a shorter period of time (i.e., 50 percent of the time period) than it is dispensed into Receivers 2 and 3. The profile of addition of Ingredient 3 into Receiver 1 is such that the shape of the dispensing rate curve is substantially symmetric. The addition profile changes for Receiver 2, wherein the rate of increase in the dispensing rate is greater than the rate of decrease in the dispensing rate. The profile of addition again changes for Receiver 3, wherein the rate of decrease in the dispensing rate is greater than the rate of increase in the dispensing rate.

Figure 13:
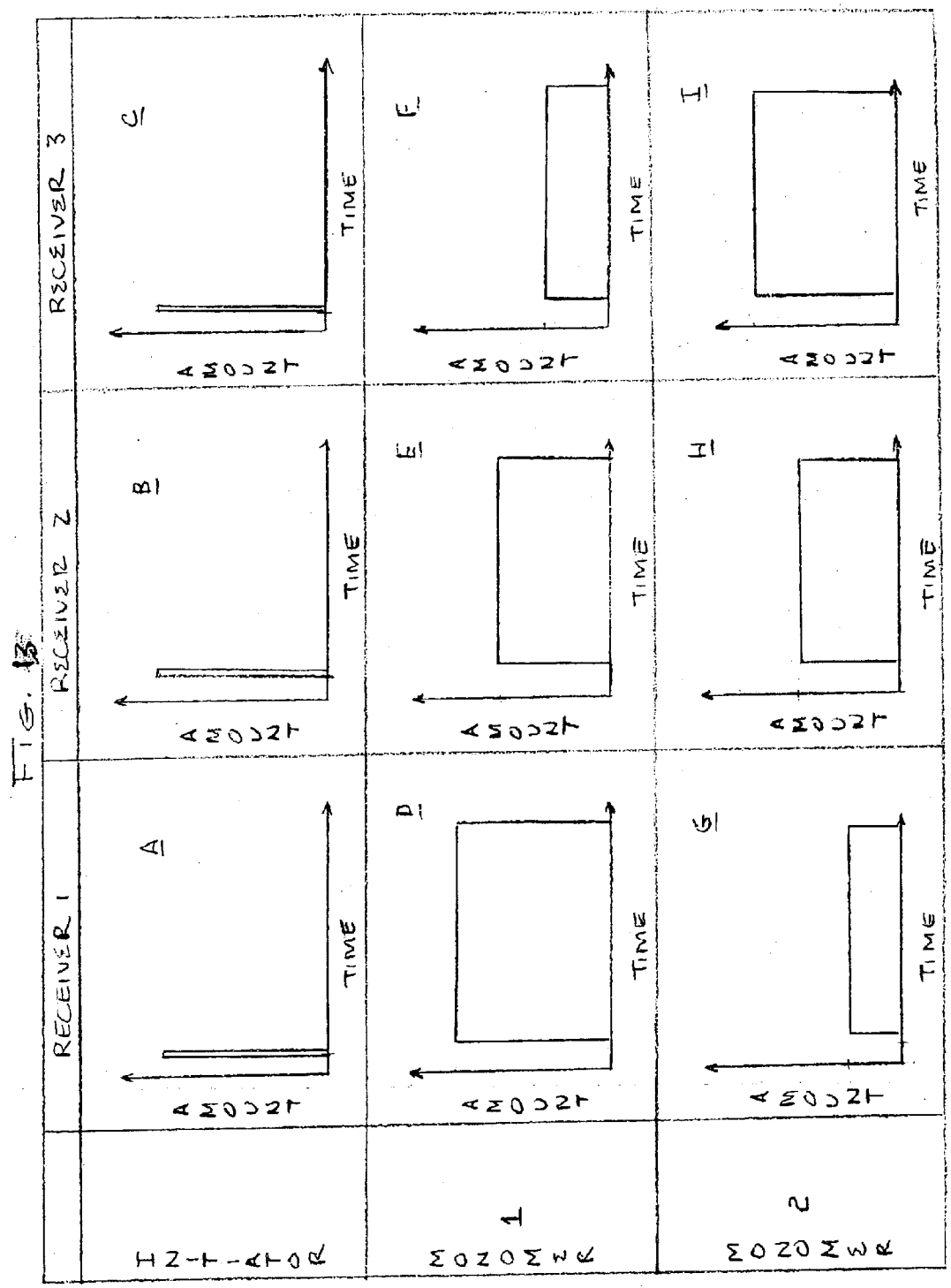
FIG. 13 depicts a second illustrative addition profile for three ingredients, which are dispensed into each of three receivers, in accordance with the protocols and methods described herein.
Figure 14:
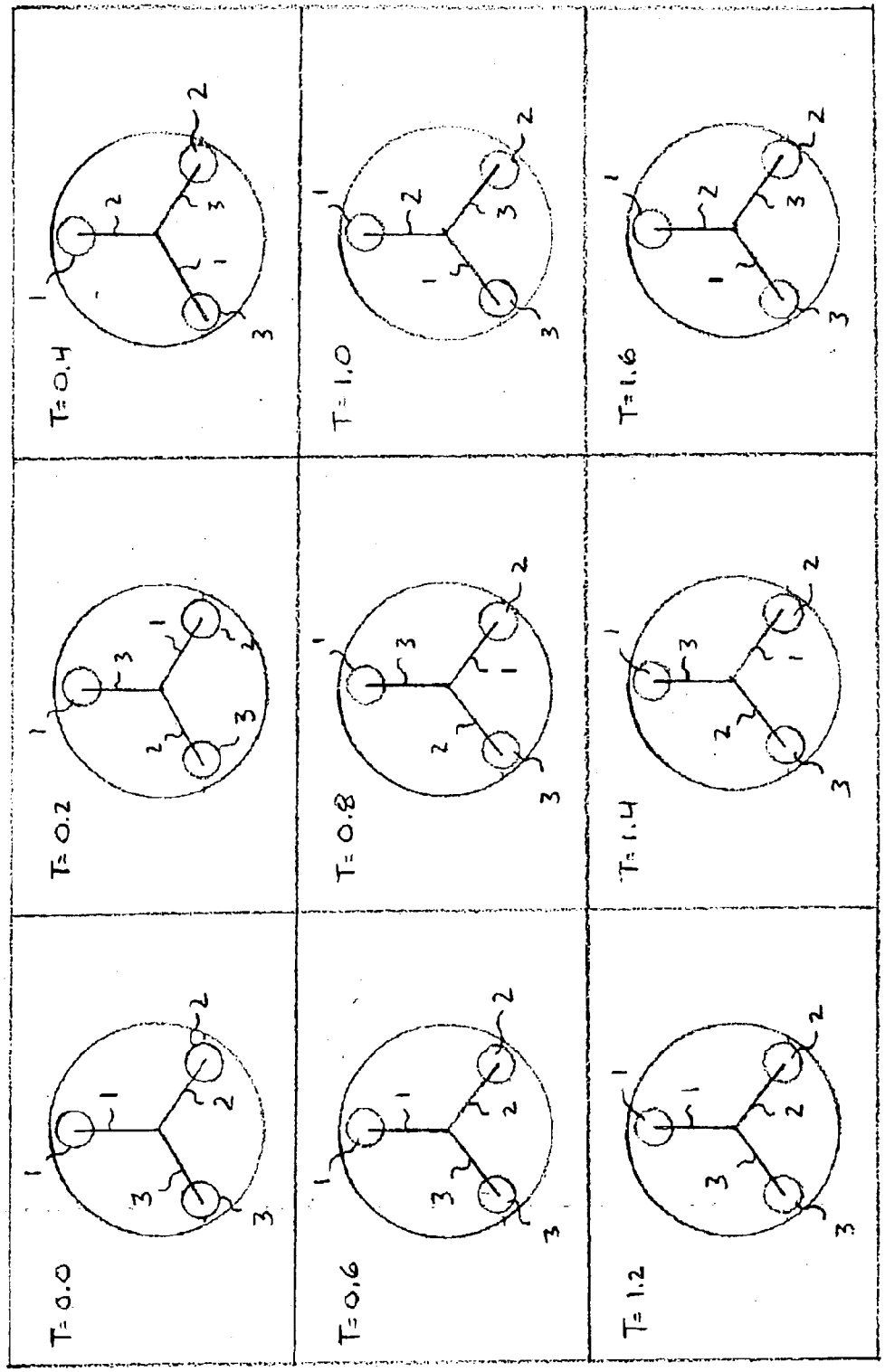
FIG. 14 depicts "snap shots" of a dispensing operation for implementing the ingredient addition profile of FIG. 13.
Figure 15:
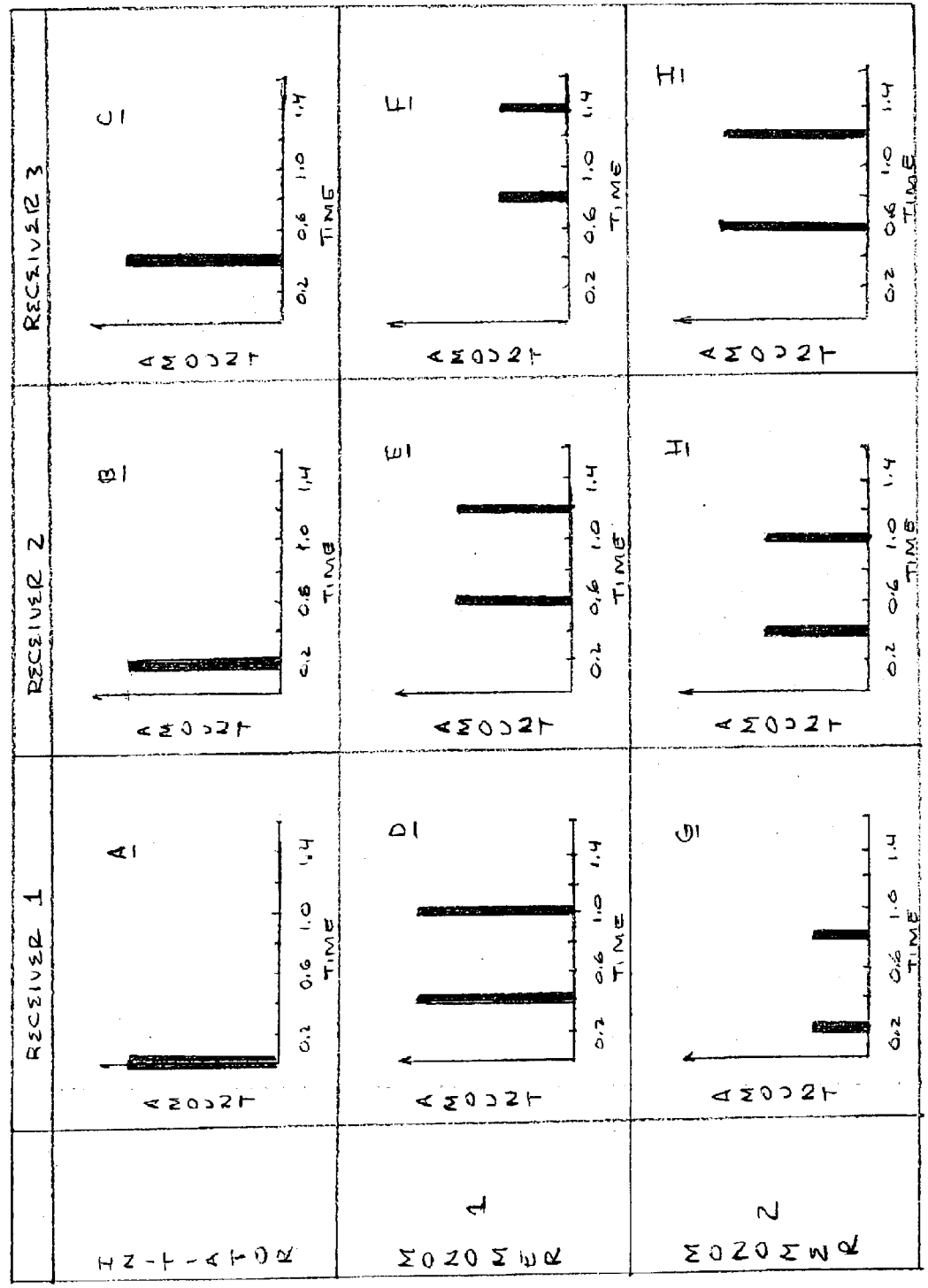
FIG. 15 depicts, for the ingredient addition profile of FIG. 13 and the dispensing operation of FIG. 14, the pulses of each ingredient per receiver over time.

FIG. 13 depicts an addition profile for three ingredients, in this case, an initiator ("Initiator") and two monomers ("Monomer 1" and "Monomer 2"), which are dispensed into each of three receivers in accordance with methods described herein. FIG. 14 depicts "snap shots" of the dispensing operation at time=0.0 seconds through time=1.6 seconds. The "circles" depicted in FIG. 14, which are identified as "1," "2," and "3" represent Receivers 1, 2 and 3. Arms "1," "2," and "3," (which terminate in dispensing elements—not shown), dispense the various ingredients into the receivers. Initiator is dispensed through Arm 1, Monomer 1 is dispensed through Arm 2, and Monomer 2 is dispensed through Arm 3. FIG. 15 depicts the pulses of each ingredient into each receiver over time.

As depicted in FIG. 13, an equal amount of Initiator is dispensed into each receiver. As shown in FIGS. 14 and 15, a pulse of Initiator is dispensed into Receiver 1 at time=0.0 seconds, a pulse of Initiator is dispensed into Receiver 2 at time=0.2 seconds, and a pulse of Initiator is dispensed into Receiver 3 at time=0.4 seconds.

As depicted in FIGS. 13, 15, and Table V below, after Initiator is dispensed into a receiver, Monomers 1 and 2 are dispensed. The dispensing rate of Monomer 1 into Receiver 1 is twice the rate of Monomer 2 into Receiver 1. The dispensing rate of Monomer 1 into Receiver 2 is equal to the rate of Monomer 2 into Receiver 2. And the dispensing rate of Monomer 1 into Receiver 3 is one-half of the rate of Monomer 2 into Receiver 3.

In this Example, the first dispensing cycle is complete after Monomer 1 is dispensed into Receiver 3. FIG. 15, and Table V below shows the time at which the first pulse of Initiator, Monomer 1 and Monomer 2 is dispensed into a given receiver.

TABLE V

The Time at which the First Pulse is Dispensed

|  | RECEIVER 1 | RECEIVER 2 | RECEIVER 3 |
| --- | --- | --- | --- |
| INITIATOR | 0.0 secs | 0.2 secs | 0.4 secs |
| MONOMER 1 | 0.4 secs | 0.6 secs | 0.8 secs |
| MONOMER 2 | 0.2 secs | 0.4 secs | 0.6 secs |

As can be seen from FIG. 15 and Table V, Initiator is dispensed into a receiver before Monomer 1 or 2 is dispensed into that receiver. But not all the Initiator is dispensed before Monomer I or II is dispensed. For example, Monomer 2 is dispensed to Receiver 1 at the same time as Initiator is dispensed to Receiver 2 and before Initiator is dispensed to Receiver 3.

FIG. 15 and Table VI below show the time at which the second pulse of Monomer I and Monomer II is dispensed into each receiver.

TABLE VI

The Time at which the Second Pulse is Dispensed

|  | RECEIVER 1 | RECEIVER 2 | RECEIVER 3 |
| --- | --- | --- | --- |
| INITIATOR | — | — | — |
| MONOMER 1 | 1.0 secs | 1.2 secs | 1.4 secs |
| MONOMER 2 | 0.8 secs | 1.0 secs | 1.2 secs |

FIG. 16 depicts a further illustrative addition profile for three ingredients, which are being dispensed into each of three receivers. The ingredients are dispensed according to the protocols that are described herein (i.e., in pulses, quasi-continuously, and quasi-simultaneously).

Receiver 1 (Plots A, D, and G)

Ingredient 2 is the first ingredient to be dispensed into Receiver 1. After a predetermined amount of Ingredient 2 is dispensed, pulsed delivery of Ingredient 2 is stopped, and an amount of Ingredient 3 is dispensed. After a predetermined amount of Ingredient 3 is dispensed, pulsed delivery of Ingredient 3 is stopped, and pulsed delivery of Ingredient 2 begins again. A first pulse of Ingredient 1 is also added to Receiver 1.

Receiver 2 (Plots B, E, and H)

Ingredient 3 is the first ingredient to be dispensed into Receiver 2. After a predetermined amount of Ingredient 3 is dispensed, pulsed delivery of Ingredient 3 is stopped, and a pulse of Ingredient 1 is dispensed, and then an amount of Ingredient 2 is dispensed. After a predetermined amount of Ingredient 2 is dispensed, pulsed delivery of Ingredient 2 is stopped, and pulsed delivery of Ingredient 3 begins again.

Receiver 3 (Plots C, F, and I)

Ingredient 2 is the first ingredient to be dispensed into Receiver 1. After a predetermined amount of Ingredient 2 is dispensed, pulsed delivery of Ingredient 2 is stopped, and an amount of Ingredient 3 is dispensed. After a predetermined amount of Ingredient 3 is dispensed, pulsed delivery of Ingredient 3 is stopped, and a pulse of ingredient 1 is dispensed. This sequence then repeats by resuming pulsed delivery of Ingredient 2, etc.

From the forgoing, it should be understood that the above-described embodiments are merely illustrative of the present invention and that many variations of the above-described embodiments can be devised by those skilled in the art without departing from the scope of the invention). It is therefore intended that such variations be included within the scope of the following claims and their equivalents.

We claim:

1. An apparatus comprising:
    a dispensing system, wherein said dispensing system has a first plurality of dispensing elements for dispensing a second plurality of ingredients into a third plurality of receivers;
    a drive system, wherein said drive system causes a relative movement between said dispensing system and said receivers to align at least one of said dispensing elements with at least one of said receivers; and
    a system controller, wherein said system controller comprises:
        means for causing said dispensing system to dispense said ingredients in a plurality of pulses; and
        means for causing said dispensing system, in conjunction with said drive system, to dispense at least some of said ingredients quasi-continuously or quasi-simultaneously or both quasi-continuously and quasi-simultaneously.

2. The apparatus of claim 1 wherein said means for causing said dispensing system to dispense at least some of said ingredients quasi-continuously or quasi-simultaneously or both quasi-continuously and quasi-simultaneously causes:
    successive pulses of an ingredient from at least one of said dispensing elements to be dispensed to different receivers; and
    successive pulses of ingredients received by at least one of said receivers to be dispensed from different dispensing elements.

3. The apparatus of claim 1 wherein a quantity of an ingredient contained in one of said pulses is about twenty percent by volume or less of a total quantity of said ingredient to be dispensed to one of said receivers.

4. The apparatus of claim 1 wherein a quantity of an ingredient contained in one of said pulses is about one percent by volume or less of a total quantity of said ingredient to be dispensed to a receiver.

5. The apparatus of claim 1 wherein said system controller further comprises:
    means for determining a quantity dispensed per pulse of each ingredient; and
    means for determining a time sequencing by which said ingredients are dispensed into each of said receivers.

6. The apparatus of claim 1 wherein said system controller further comprises means for determining a quantity dispensed per pulse for each ingredient per receiver.

7. The apparatus of claim 1 wherein said means for causing said dispensing system to dispense at least some of said ingredients quasi-continuously or quasi-simultaneously or both quasi-continuously and quasi-simultaneously causes said receivers to receive one pulse of each of said ingredients, thereby defining a dispensing cycle, before receiving a second pulse of any of said ingredients.

8. The apparatus of claim 7 wherein said dispensing cycle is completed in one second or less.

9. The apparatus of claim 7 wherein said dispensing cycle is completed in five seconds or less.

10. The apparatus of claim 1 wherein said means for causing said dispensing system to dispense at least some of said ingredients quasi-continuously or quasi-simultaneously or both quasi-continuously and quasi-simultaneously causes successive pulses of any one ingredient to be received by a receiver in one second or less.

11. The apparatus of claim 1 wherein said means for causing said dispensing system to dispense at least some of said ingredients quasi-continuously or quasi-simultaneously or both quasi-continuously and quasi-simultaneously causes successive pulses of any one ingredient to be received by a receiver in five seconds or less.

12. The apparatus of claim 1 wherein a ratio of a number, n, of said dispensing elements to a number, m, of said ingredients to be dispensed is 1.

13. The apparatus of claim 1 wherein said drive system moves said dispensing system.

14. The apparatus of claim 13 wherein said drive system creates rotary motion.

15. The apparatus of claim 1 wherein there are at least five dispensing elements in said first plurality of dispensing elements.

16. The apparatus of claim 1 wherein there are at least five ingredients in said second plurality of ingredients.

17. The apparatus of claim 1 wherein there are at least eight receivers in said third plurality of receivers.

18. A method for producing a mixture of a first plurality of ingredients in a second plurality of receivers, the method comprising:
    dispensing said ingredients as a plurality of pulses, wherein each pulse contains some but not all of a respective one of said ingredients; and
    sequencing said plurality of pulses so that said dispensing of at least some of said ingredients is quasi-simultaneous.

19. The method of claim 18 wherein the operation of sequencing further comprises sequencing said plurality of pulses so that said dispensing of at least one of said ingredients is quasi-continuous.

20. The method of claim 18 wherein said operation of sequencing further comprises sequencing said plurality of pulses so that, for at least one of said ingredients, successive pulses of said one ingredient are dispensed to different receivers.

21. The method of claim 18 wherein said operation of sequencing further comprises sequencing said plurality of pulses so that successive pulses received by one of said receivers comprise different ingredients.

22. The method of claim 18 wherein said operation of sequencing further comprises sequencing said plurality of pulses so that all ingredients are added to a given receiver within 5 seconds.

23. The method of claim 18 wherein said operation of sequencing further comprises sequencing said plurality of pulses so that at least one of said ingredients is added to said second plurality of receivers within 5 seconds.

24. The method of claim 18 wherein said operation of sequencing further comprises sequencing said plurality of pulses so that all ingredients are added to said second plurality of receivers within 5 seconds.

25. The method of claim 18 wherein said operation of sequencing further comprises sequencing said plurality of pulses so that all ingredients are added to a given receiver within 100 seconds.

26. The method of claim 18 wherein said operation of sequencing further comprises sequencing said plurality of pulses so that at least one of said ingredients is added to said second plurality of receivers within 100 seconds.

27. The method of claim 18 wherein said operation of sequencing further comprises sequencing said plurality of pulses so that all ingredients are added to said second plurality of receivers within 100 seconds.

28. The method of claim 19 wherein said operation of sequencing further comprises sequencing said plurality of pulses so that, for at least one of said ingredients, each receiver receives one pulse of said one ingredient before any of said receivers receives a second pulse said one ingredient.

29. The method of claim 19 wherein said operation of sequencing further comprises sequencing said plurality of pulses so that said second pulse is received within 5 seconds of said first pulse.

30. The method of claim 19 wherein said operation of sequencing further comprises sequencing said plurality of pulses so that said second pulse is received within 100 seconds of said first pulse.

31. The method of claim 18 wherein said operation of dispensing further comprises dispensing said ingredients as a plurality of pulses, wherein, for at least one of said ingredients, each pulse contains less than 1 percent of a total amount of said one ingredient that is to be delivered to any one of said receivers.

32. A method for producing a mixture of a first plurality of ingredients in a second plurality of receivers, the method comprising:

determining an execution sequence for dispensing said ingredients based on a dispensing protocol, wherein:
said dispensing protocol comprises dispensing said ingredients as a plurality of pulses, wherein each pulse contains some but not all of a respective one of said ingredients to be dispensed to any one of said receivers; and
said execution sequence comprises:
a quantity of ingredient dispensed for each pulse into each of said receivers for each of said ingredients;
a sequencing of pulses for each of said ingredients for each of said receivers; and dispensing said ingredients into said receivers in accordance with said execution sequence.

33. The method of claim 32 wherein said quantity of ingredient dispensed for each pulse into each of said receivers changes.

34. The method of claim 32 wherein, for at least one of said ingredients, each pulse contains less than 1 percent of a total amount of said one ingredient that is to be delivered to any one of said receivers.

\* \* \* \* \*